US00RE50681E

(19) United States
(12) Reissued Patent
Payne et al.

(10) Patent Number: US RE50,681 E
(45) **Date of Reissued Patent: *Dec. 2, 2025**

(54) IONIZABLE CATIONIC LIPID FOR RNA DELIVERY

(71) Applicant: Arcturus Therapeutics, Inc., San Diego, CA (US)

(72) Inventors: Joseph E. Payne, San Diego, CA (US); Padmanabh Chivukula, San Diego, CA (US)

(73) Assignee: Arcturus Therapeutics, Inc, San Diego, CA (US)

( * ) Notice: This patent is subject to a terminal disclaimer.

(21) Appl. No.: 17/958,932

(22) Filed: Oct. 3, 2022

Related U.S. Patent Documents

Reissue of:
(64) Patent No.: 9,593,077
Issued: Mar. 14, 2017
Appl. No.: 14/546,105
Filed: Nov. 18, 2014

U.S. Applications:
(63) Continuation of application No. 16/351,301, filed on Mar. 12, 2019, now Pat. No. Re. 49,233, which is an application for the reissue of Pat. No. 9,593,077.

(60) Provisional application No. 61/905,724, filed on Nov. 18, 2013.

(51) Int. Cl.

| | |
|---|---|
| ***C07C 323/52*** | (2006.01) |
| ***A61K 47/18*** | (2017.01) |
| ***A61K 47/20*** | (2006.01) |
| ***C07C 235/12*** | (2006.01) |
| ***C07C 237/12*** | (2006.01) |
| ***C07C 271/22*** | (2006.01) |
| ***C07C 323/25*** | (2006.01) |
| ***C07C 323/60*** | (2006.01) |
| ***C07C 333/04*** | (2006.01) |
| ***C07J 41/00*** | (2006.01) |
| ***C11C 3/04*** | (2006.01) |
| ***C12N 15/11*** | (2006.01) |
| ***C12N 15/113*** | (2010.01) |

(52) U.S. Cl.
CPC ..... *C07C 323/52* (2013.01); *A61K 47/18* (2013.01); *A61K 47/20* (2013.01); *C07C 235/12* (2013.01); *C07C 237/12* (2013.01); *C07C 271/22* (2013.01); *C07C 323/25* (2013.01); *C07C 323/60* (2013.01); *C07C 333/04* (2013.01); *C07J 41/0055* (2013.01); *C11C 3/04* (2013.01); *C12N 15/111* (2013.01); *C12N 15/113* (2013.01); *C12N 15/1137* (2013.01); *C12N 2310/14* (2013.01); *C12N 2320/32* (2013.01)

(58) Field of Classification Search
CPC ... C07C 323/52; C07C 235/12; C07C 237/12; C07C 271/22; C07C 323/25; C07C 323/60; C07C 333/04; A61K 47/18; A61K 47/20; C07J 41/0055; C11C 3/04; C12N 15/111; C12N 15/113; C12N 15/1137; C12N 2310/14; C12N 2320/32; A61P 35/00; A61P 29/00
See application file for complete search history.

(56) References Cited

U.S. PATENT DOCUMENTS

| | | | | |
|---|---|---|---|---|
| 4,511,069 | A | 4/1985 | Kalat | |
| 4,778,810 | A | 10/1988 | Wenig et al. | |
| 5,849,902 | A | 12/1998 | Arrow et al. | |
| 9,011,903 | B2 | 4/2015 | Niitsu et al. | |
| 9,365,610 | B2 * | 6/2016 | Payne | C12N 15/113 |

(Continued)

FOREIGN PATENT DOCUMENTS

| | | | |
|---|---|---|---|
| CA | 2876148 | A1 | 12/2013 |
| CA | 2837101 | C | 12/2020 |

(Continued)

OTHER PUBLICATIONS

Zaragoza Dorwald, Side Reactions in Organic Synthesis, 2005, WILEY-VCH Verlag GmbH & Co. KGaA, Weinheim, Preface. p. IX.*

(Continued)

*Primary Examiner* — Alan D Diamond
(74) *Attorney, Agent, or Firm* — BakerHostetler

(57) ABSTRACT

What is described is a compound of formula (1)

1 wherein $R_1$ and $R_2$ are the same or different, each a linear or branched alkyl with 1-9 carbons, or an alkenyl or alkynyl with 2 to 11 carbon atoms;

$L_1$ and $L_2$ are the same or different, each a linear alkyl having 5 to 18 carbon atoms, or form a heterocycle with N;

$X_1$ is a bond, or is —CO—O— whereby $L_2$-CO—O—$R_2$ is formed;

$X_2$ is S or O; $L_3$ is a bond or a lower alkyl, or form a heterocycle with N;

$R_3$ is a lower alkyl; and $R_4$ and $R_5$ are the same or different, each a lower alkyl;

or a pharmaceutically acceptable salt thereof.

15 Claims, 4 Drawing Sheets

(56) References Cited

U.S. PATENT DOCUMENTS

| | | | | |
|---|---|---|---|---|
| 9,567,296 | B2 * | 2/2017 | Payne | A61K 47/18 |
| 9,580,711 | B2 * | 2/2017 | Payne | C07C 271/22 |
| 9,670,152 | B2 * | 6/2017 | Payne | A61K 47/20 |
| 9,834,510 | B2 * | 12/2017 | Payne | C07C 271/22 |
| 9,850,202 | B2 | 12/2017 | Payne et al. | |
| 9,896,413 | B2 * | 2/2018 | Payne | C07C 271/22 |
| 9,951,002 | B2 | 4/2018 | Payne et al. | |
| 10,383,952 | B2 * | 8/2019 | Payne | A61P 31/00 |
| 10,526,284 | B2 | 1/2020 | Payne et al. | |
| 10,781,169 | B2 * | 9/2020 | Payne | A61K 47/20 |
| 10,961,188 | B2 | 3/2021 | Payne et al. | |
| 10,961,895 | B2 | 3/2021 | Higashino et al. | |
| 10,980,895 | B2 | 4/2021 | Payne et al. | |
| RE49,233 | E * | 10/2022 | Payne | C11C 3/04 |
| 2012/0027803 | A1 | 2/2012 | Manoharan et al. | |
| 2013/0022665 | A1 | 1/2013 | Niitsu et al. | |
| 2013/0129811 | A1 | 5/2013 | Kuboyama et al. | |
| 2013/0274504 | A1 | 10/2013 | Colletti et al. | |
| 2013/0280305 | A1 | 10/2013 | Kuboyama et al. | |
| 2013/0330401 | A1 | 12/2013 | Payne et al. | |

FOREIGN PATENT DOCUMENTS

| | | | |
|---|---|---|---|
| CN | 105873902 | A | 8/2016 |
| EP | 1502576 | A2 | 2/2005 |
| FR | 1481016 | A | 5/1967 |
| JP | 61-089286 | | 5/1986 |
| JP | 61-136584 | | 6/1986 |
| JP | 2016-538343 | A | 12/2016 |
| WO | WO 92/07065 | A1 | 4/1992 |
| WO | WO 1992/07065 | A1 | 4/1992 |
| WO | WO 93/15187 | A1 | 8/1993 |
| WO | WO 1993/15187 | A1 | 8/1993 |
| WO | WO 2010/061880 | A1 | 6/2010 |
| WO | WO 2011/136368 | A1 | 11/2011 |
| WO | WO 2011/153493 | A2 | 12/2011 |
| WO | WO 2012/170952 | A2 | 12/2012 |
| WO | WO 2012/170952 | A9 | 12/2012 |
| WO | WO 2013/065825 | A1 | 5/2013 |
| WO | WO 2013/086373 | A1 | 6/2013 |
| WO | WO 2013/185116 | A1 | 12/2013 |
| WO | WO 2015/074085 | A1 | 5/2015 |
| WO | WO 2016/081029 | A1 | 5/2016 |

OTHER PUBLICATIONS

Reusch, Virtual Textbook in Organic Chemistry, Heterocyclic Compounds, 1999, p. 5, Recovered from https://www2.chemistry.msu.edu/faculty/reusch/virttxtjml/ heterocy.htm.*

International Patent Application No. PCT/US2014/066242; Int'l Search Report and the Written Opinion; dated Feb. 10, 2015; 10 pages.

* cited by examiner

IONIZABLE CATIONIC LIPID FOR RNA DELIVERY

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS REFERENCE TO RELATED APPLICATIONS

This application *is a reissue of U.S. patent application Ser. No. 14/546,105, filed Nov. 18, 2014, issued as U.S. Pat. No. RE49,233, and is a continuation of U.S. patent application Ser. No. 16/351,301, filed Mar. 12, 2019, which is a reissue of U.S. patent application Ser. No. 14/546,105, filed Nov. 18, 2014, which* claims benefit under 35 U.S.C. § 119(e) of [Provisional] U.S. [patent application] *Provisional Patent Application* No. 61/905,724, filed Nov. 18, 2013, the contents of which is incorporated herein by reference in its entirety.

BACKGROUND

A number of different types of nucleic acids are currently being developed as therapeutics for the treatment of a number of diseases. These nucleic acids include DNA in gene therapy, plasmids-based interfering nucleic acids, small interfering nucleic acids for use in RNA interference (RNAi), including siRNA, miRNA, antisense molecules, ribozymes and aptamers. As these molecules are being developed, there has been developed a need to produce them in a form that is stable and has a long shelf-life and that can be easily incorporated into an anhydrous organic or anhydrous polar aprotic solvent to enable encapsulations of the nucleic acids without the side-reactions that can occur in a polar aqueous solution or nonpolar solvents.

The present invention relates to novel lipid compositions that facilitate the intracellular delivery of biologically active and therapeutic molecules. The present invention relates also to pharmaceutical compositions that comprise such lipid compositions, and that are useful to deliver therapeutically effective amounts of biologically active molecules into the cells of patients.

The delivery of a therapeutic compound to a subject is important for its therapeutic effects and usually it can be impeded by limited ability of the compound to reach targeted cells and tissues. Improvement of such compounds to enter the targeted cells of tissues by a variety of the means of delivery is crucial. The present invention relates the novel lipids, incompositions and methods for preparation that facilitate the targeted intracellular delivery of biological active molecules.

Examples of biologically active molecules for which effective targeting to a patient's tissues is often not achieved include: (1) numerous proteins including immunoglobin proteins, (2) polynucleotides such as genomic DNA, cDNA, or mRNA (3) antisense polynucleotides; and (4) many low molecular weight compounds, whether synthetic or naturally occurring, such as the peptide hormones and antibiotics.

One of the fundamental challenges now facing medical practitioners is that a number of different types of nucleic acids are currently being developed as therapeutics for the treatment of a number of diseases. These nucleic acids include DNA in gene therapy, plasmids small interfering nucleic acids (iNA) for use in RNA interference (RNAi), antisense molecules, ribozymes, antagomirs, microRNA and aptamers. As these nucleic are being developed, there is a need to produce lipid formulations that are easy to make and can be readily delivered to a target tissue.

SUMMARY

What is described herein is a compound of Formula 1

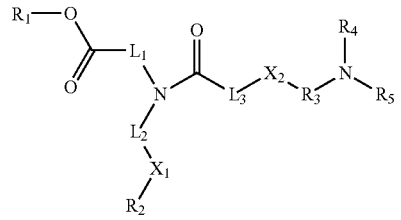

1 in which $R_1$ and $R_2$ are the same or different, each a linear or branched alkyl, alkenyl, or alkynyl, $L_1$ and $L_2$ are the same or different, each a linear alkyl having at least five carbon atoms, or form a heterocycle with the N, $X_1$ is a bond, or is —CO—O— whereby $L_2$-CO—O—$R_2$ is formed $X_2$ is S or O, $L_3$ is a bond or a lower alkyl, $R_3$ is a lower alkyl, $R_4$ and $R_5$ are the same or different, each a lower alkyl.

What is also described herein is the compound of formula 1, in which $L_3$ is absent, $R_1$ and $R_2$ each consists of at least seven carbon atoms, $R_3$ is ethylene or n-propylene, $R_4$ and $R_5$ are methyl or ethyl, and $L_1$ and $L_2$ each consists of a linear alkyl having at least five carbon atoms.

What is also described herein is the compound of formula 1, in which $L_3$ is absent, $R_1$ and $R_2$ each consists of at least seven carbon atoms, $R_3$ is ethylene or n-propylene, $R_4$ and $R_5$ are methyl or ethyl, and $L_1$ and $L_2$ each consists of a linear alkyl having at least five carbon atoms.

What is also described herein is the compound of formula 1, in which $L_3$ is absent, $R_1$ and $R_2$ each consists of an alkenyl of at least nine carbon atoms, $R_3$ is ethylene or n-propylene, $R_4$ and $R_5$ are methyl or ethyl, and $L_1$ and $L_2$ each consists of a linear alkyl having at least five carbon atoms.

What is also described herein is the compound of formula 1, in which $L_3$ is methylene, $R_1$ and $R_2$ each consists of at least seven carbon atoms, $R_3$ is ethylene or n-propylene, $R_4$ and $R_5$ are methyl or ethyl, and $L_1$ and $L_2$ each consists of a linear alkyl having at least five carbon atoms.

What is also described herein is the compound of formula 1, in which $L_3$ is methylene, $R_1$ and $R_2$ each consists of at least nine carbon atoms, $R_3$ is ethylene or n-propylene, $R_4$ and $R_5$ are each methyl, $L_1$ and $L_2$ each consists of a linear alkyl having at least seven carbon atoms.

What is also described herein is the compound of formula 1, in which $L_3$ is methylene, $R_1$ consists of an alkenyl having at least nine carbon atoms and $R_2$ consists of an alkenyl having at least seven carbon atoms, $R_3$ is n-propylene, $R_4$ and $R_5$ are each methyl, $L_1$ and $L_2$ each consists of a linear alkyl having at least seven carbon atoms.

What is also described herein is the compound of formula 1, in which $L_3$ is methylene, $R_1$ and $R_2$ each consists of an alkenyl having at least nine carbon atoms, $R_3$ is ethylene, $R_4$ and $R_5$ are each methyl, $L_1$ and $L_2$ each consists of a linear alkyl having at least seven carbon atoms.

What is also described herein is a compound having the structure
ATX-001
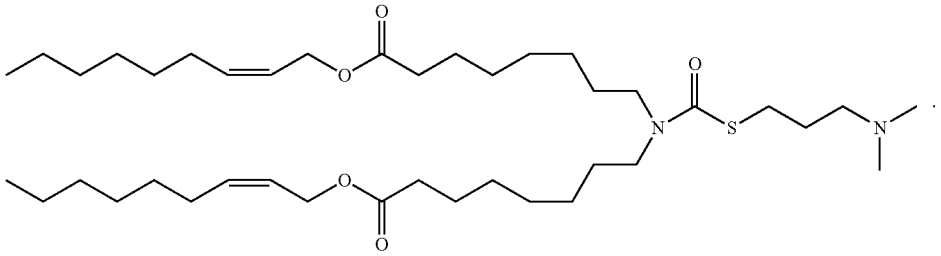
What is also described herein is a compound having the structure
ATX-002
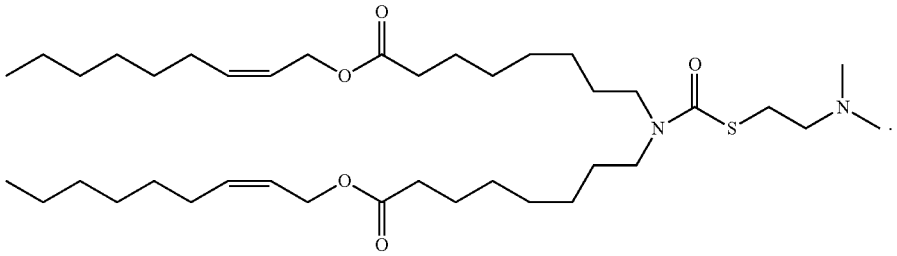
What is also described herein is a compound having the structure
ATX-003
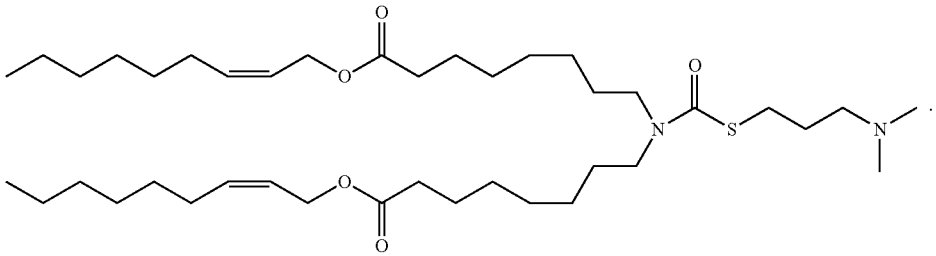
What is also described herein is a compound having the structure
ATX-004
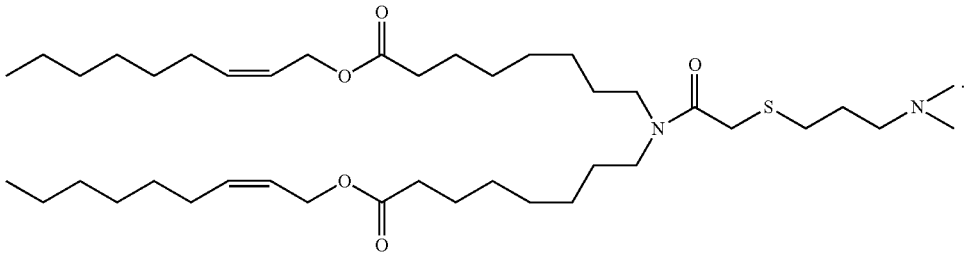

What is also described herein is a compound having the structure
ATX-005
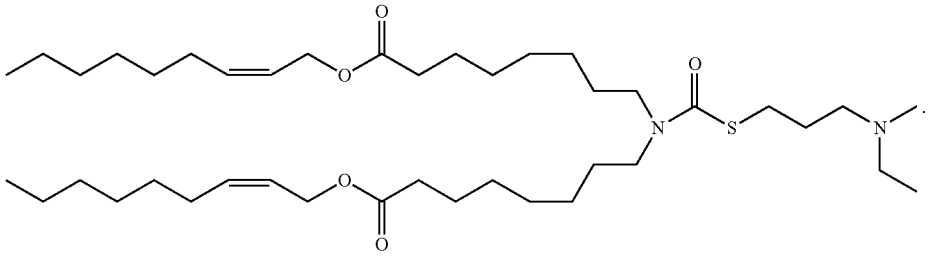
What is also described herein is a compound having the structure
ATX-006
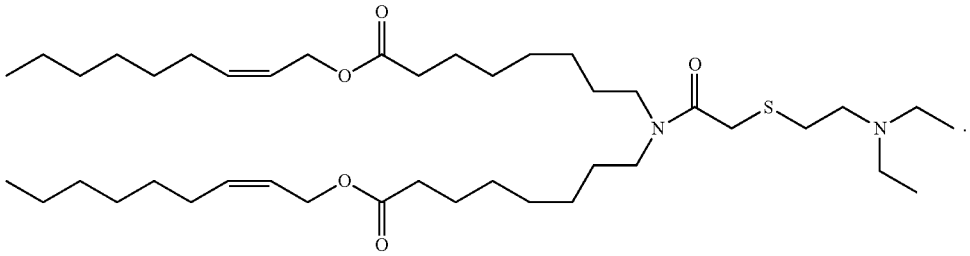
What is also described herein is a compound having the structure
ATX-007
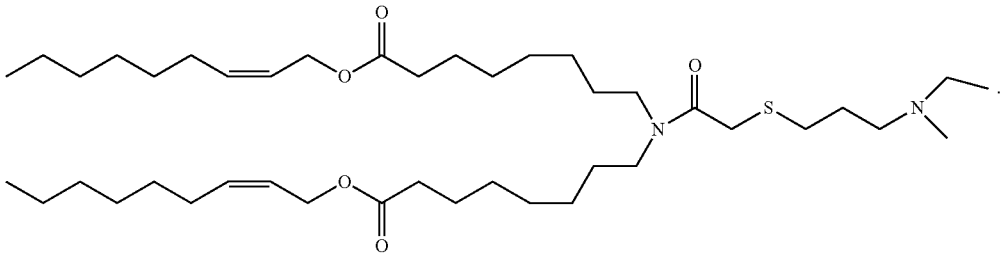
What is also described herein is a compound having the structure
ATX-008
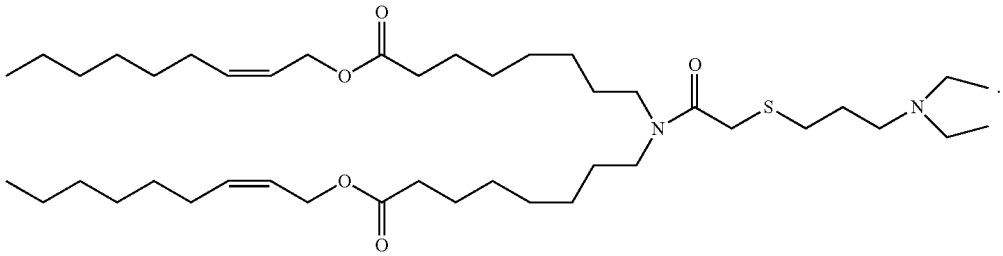

What is also described herein is a compound having the structure
ATX-009
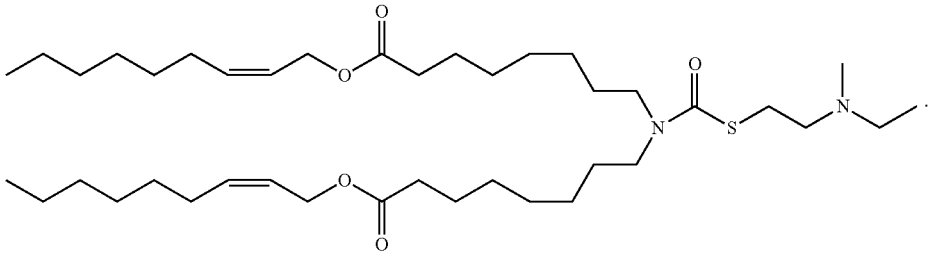
What is also described herein is a compound having the structure
ATX-010
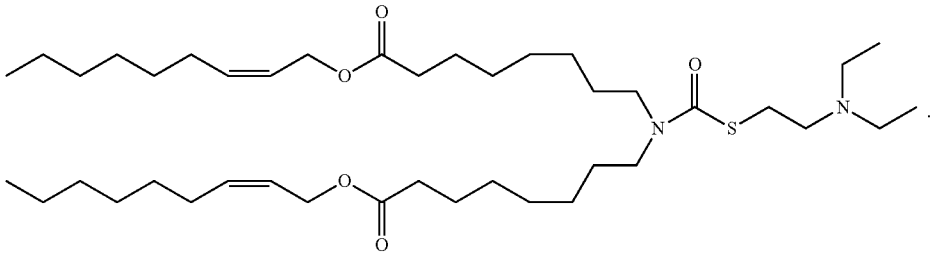
What is also described herein is a compound having the structure
ATX-011
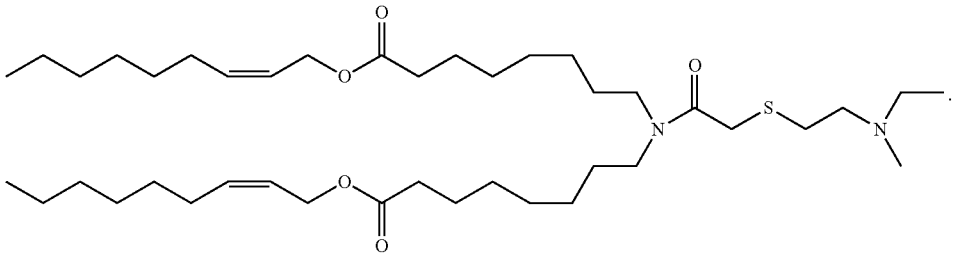
What is also described herein is a compound having the structure
ATX-012
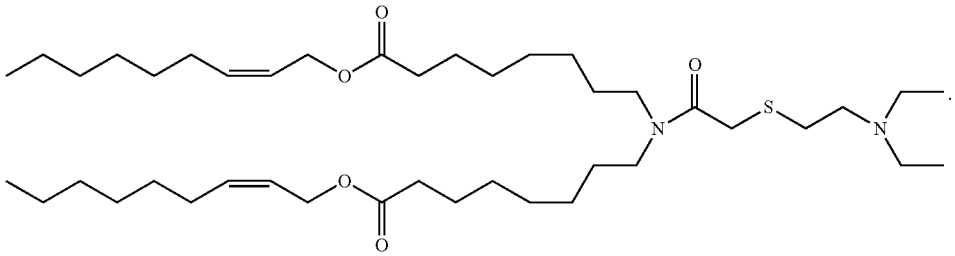

What are also described herein are any of the compounds listed in ATX-001 to ATX-032 listed in Table 1, below, or a pharmaceutically acceptable salt thereof, in a lipid composition, comprising a nanoparticle or a bilayer of lipid molecules. The lipid bilayer preferably further comprises a neutral lipid or a polymer. The lipid composition preferably comprises a liquid medium. The composition preferably further encapsulates a nucleic acid. The nucleic acid preferably has an activity of suppressing the expression of the target gene by utilizing RNA interference (RNAi). The lipid composition preferably further comprises a nucleic acid and a neutral lipid or a polymer. The lipid composition preferably encapsulates the nucleic acid.

The nucleic acid preferably has an activity of suppressing the expression of a target gene. The target gene preferably is a gene associated with inflammation.

What is also described herein is a method for introducing a nucleic acid into a cell of a mammal by using any of the compositions, above. The cell may be in a liver, lung, kidney, brain, blood, spleen, or bone. The composition preferably is administered intravenously, subcutaneously, intraperitoneally, or intrathecally. Preferably, the compositions described herein are used in a method for treating cancer or inflammatory disease. The disease may be one selected from the group consisting of immune disorder, cancer, renal disease, fibrotic disease, genetic abnormality, inflammation, and cardiovascular disorder.

DETAILED DESCRIPTION OF ILLUSTRATIVE EMBODIMENTS

Figure 1:
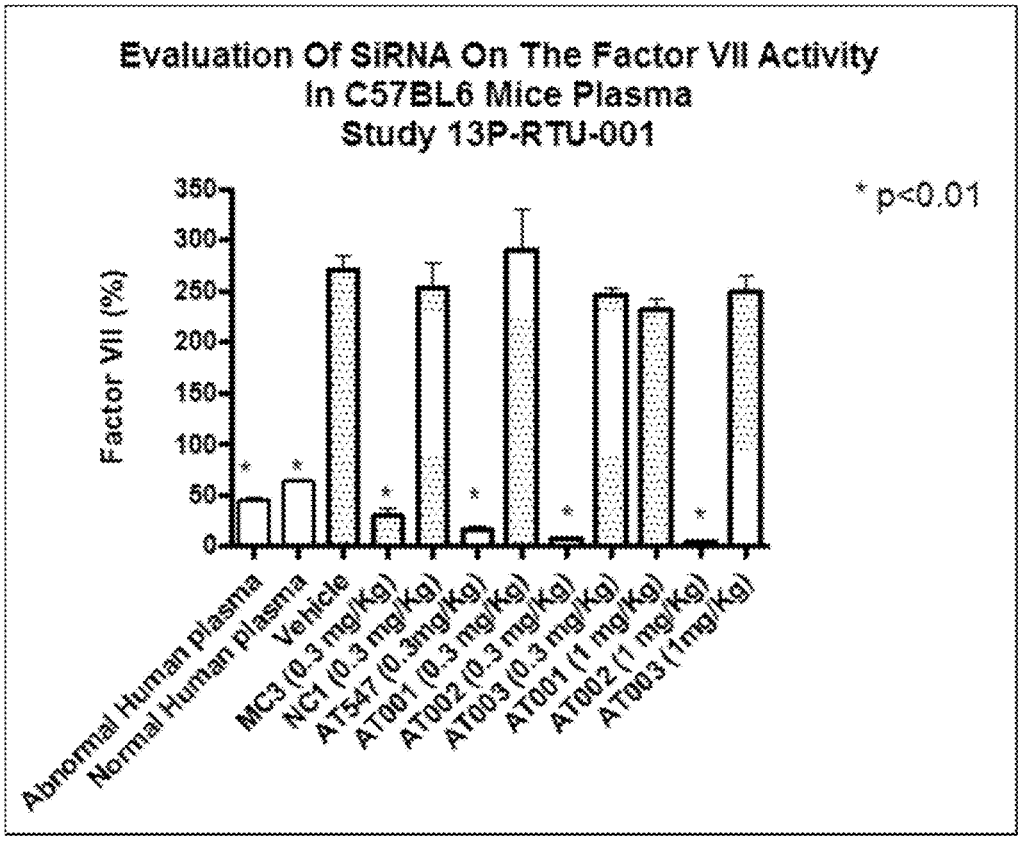
FIG. 1 shows the knockdown activity of siRNA encapsulated by different cationic lipids. The lipids include MC3 (0.3 mg/kg), NC1 (0.3 mg/kg), ATX-547 (0.3 mg/kg), ATX-001 (0.3 and 1.0 mg/kg), ATX-002 (0.3 and 1.0 mg/kg), and ATX-003 (0.3 and 1.0 mg/kg). The amount of Factor VII knockdown in mouse plasma is shown following administration of the siRNA formulation to C57BL6 mice, compared to injection of vehicle alone. The amount of Factor VII in abnormal and normal human plasma is included as a control. Statistically significant decreases in Factor VII levels ($p<0.01$) is shown by an asterix (*).

"At least one" means one or more (e.g., 1-3, 1-2, or 1).

"Composition" includes a product comprising the specified ingredients in the specified amounts, as well as any product that results, directly or indirectly, from combination of the specified ingredients in the specified amounts.

"In combination with" as used to describe the administration of a compound of formula (1) with other medicaments in the methods of treatment of this invention, means-that the compounds of formula (1) and the other medicaments are administered sequentially or concurrently in separate dosage forms, or are administered concurrently in the same dosage form.

"Mammal" means a human or other mammal, or means a human being.

"Patient" includes both human and other mammals, preferably human.

"Alkyl" is a saturated or unsaturated, straight or branched, hydrocarbon chain. In various embodiments, the alkyl group has 1-18 carbon atoms, i.e. is a $C_1$-$C_{18}$ group, or is a $C_1$-$C_{12}$ group, a $C_1$-$C_6$ group, or a $C_1$-$C_4$ group. Independently, in various embodiments, the alkyl group has zero branches (i.e., is a straight chain), one branch, two branches, or more than two branches. "Alkenyl" is an unsaturated alkyl that may have one double bond, two double bonds, more than two double bonds. "Alkynal" is an unsaturated alkyl that may have one triple bond, two triple bonds, or more than two triple bonds. Alkyl chains may be optionally substituted with 1 substituent (i.e., the alkyl group is mono-substituted), or 1-2 substituents, or 1-3 substituents, or 1-4 substituents, etc. The substituents may be selected from the group consisting of hydroxy, amino, alkylamino, boronyl, carboxy, nitro, cyano, and the like. When the alkyl group incorporates one or more heteroatoms, the alkyl group is referred to herein as a heteroalkyl group. When the substituents on an alkyl group are hydrocarbons, then the resulting group is simply referred to as a substituted alkyl. In various aspects, the alkyl group including substituents has less than 25, 24, 23, 22, 21, 20, 19, 18, 17, 16, 15, 14, 13, 12, 11, 10, 9, 8, or 7 carbons.

"Lower alkyl" means a group having about one to about six carbon atoms in the chain which chain may be straight or branched. Non-limiting examples of suitable alkyl groups include methyl, ethyl, n-propyl, isopropyl, n-butyl, t-butyl, n-pentyl, and hexyl.

"Alkoxy" means an alkyl-O-group wherein alkyl is as defined above. Non-limiting examples of alkoxy groups include: methoxy, ethoxy, n-propoxy, isopropoxy, n-butoxy and heptoxy. The bond to the parent moiety is through the ether oxygen.

"Alkoxyalkyl" means an alkoxy-alkyl-group in which the alkoxy and alkyl are as previously described. Preferred alkoxyalkyl comprise a lower alkyl group. The bond to the parent moiety is through the alkyl.

"Alkylaryl" means an alkyl-aryl-group in which the alkyl and aryl are as previously described. Preferred alkylaryls comprise a lower alkyl group. The bond to the parent moiety is through the aryl.

"Aminoalkyl" means an $NH_2$-alkyl-group, wherein alkyl is as defined above, bound to the parent moiety through the alkyl group.

"Carboxyalkyl" means an HOOC-alkyl-group, wherein alkyl is as defined above, bound to the parent moiety through the alkyl group.

"Commercially available chemicals" and the chemicals used in the Examples set forth herein may be obtained from standard commercial sources, where such sources include, for example, Acros Organics (Pittsburgh, Pa.), Sigma-Adrich Chemical (Milwaukee, Wis.), Avocado Research (Lancashire, U.K.), Bionet (Cornwall, U.K.), Boron Molecular (Research Triangle Park, N.C.), Combi-Blocks (San Diego, Calif.), Eastman Organic Chemicals, Eastman Kodak Company (Rochester, N.Y.), Fisher Scientific Co. (Pittsburgh, Pa.), Frontier Scientific (Logan, Utah), ICN Biomedicals, Inc. (Costa Mesa, Calif.), Lancaster Synthesis (Windham, N.H.), Maybridge Chemical Co. (Cornwall, U.K.), Pierce Chemical Co. (Rockford, Ill.), Riedel de Haen (Hannover, Germany), Spectrum Quality Product, Inc. (New Brunswick, N.J.), TCI America (Portland, Oreg.), and Wako Chemicals USA, Inc. (Richmond, Va.).

"Compounds described in the chemical literature" may be identified through reference books and databases directed to chemical compounds and chemical reactions, as known to one of ordinary skill in the art. Suitable reference books and treatise that detail the synthesis of reactants useful in the preparation of compounds disclosed herein, or provide references to articles that describe the preparation of compounds disclosed herein, include for example, "Synthetic Organic Chemistry", John Wiley and Sons, Inc. New York; S. R. Sandler et al, "Organic Functional Group Preparations," $2^{nd}$ Ed., Academic Press, New York, 1983; H. O. House, "Modern Synthetic Reactions," $2^{nd}$ Ed., W. A. Benjamin, Inc. Menlo Park, Calif., 1972; T. L. Glichrist, "Heterocyclic Chemistry," $2^{nd}$ Ed. John Wiley and Sons, New York, 1992; J. March, "Advanced Organic Chemistry: reactions, Mechanisms and Structure," $5^{th}$ Ed., Wiley Interscience, New York, 2001; Specific and analogous reactants may also be identified through the indices of known chemicals prepared by the Chemical Abstract Service of the American Chemical Society, which are available in most public and university libraries, as well as through online databases (the American Chemical Society, Washington, D.C. may be contacted for more details). Chemicals that are known but not commercially available in catalogs may be prepared by custom chemical synthesis houses, where many of the standard chemical supply houses (such as, those listed above) provide custom synthesis services.

"Halo" means fluoro, chloro, bromo, or iodo groups. Preferred are fluoro, chloro or bromo, and more preferred are fluoro and chloro.

"Halogen" means fluorine, chlorine, bromine, or iodine. Preferred are fluorine, chlorine and bromine.

"Heteroalkyl" is a saturated or unsaturated, straight or branched, chain containing carbon and at least one heteroatom. The heteroalkyl group may, in various embodiments, have on heteroatom, or 1-2 heteroatoms, or 1-3 heteroatoms, or 1-4 heteroatoms. In one aspect the heteroalkyl chain contains from 1 to 18 (i.e., 1-18) member atoms (carbon and heteroatoms), and in various embodiments contain 1-12, or 1-6, or 1-4 member atoms. Independently, in various embodiments, the heteroalkyl group has zero branches (i.e., is a straight chain), one branch, two branches, or more than two branches. Independently, in one embodiment, the hetereoalkyl group is saturated. In another embodiment, the heteroalkyl group is unsaturated. In various embodiments, the unsaturated heterolkyl may have one double bond, two double bonds, more than two double bonds, and/or one triple bond, two triple bonds, or more than two triple bonds. Heteroalkyl chains may be substituted or unsubstituted. In one embodiment, the heteroalkyl chain is unsubstituted. In another embodiment, the heteroalkyl chain is substituted. A substituted heteroalkyl chain may have 1 substituent (i.e., by monosubstituted), or may have 1-2 substituents, or 1-3 substituents, or 1-4 substituents, etc. Exemplary heteroalkyl substituents include esters (—C(O)—O—R) and carbonyls (—C(O)—).

"Hydroxyalkyl" means an HO-alkyl-group, in which alkyl is previously defined. Preferred hydroxyalkyls contain lower alkyl. Non-limiting examples of suitable hydroxyalkyl groups include hydroxymethyl and 2-hydroxyethyl.

"Hydrate" is a solvate wherein the solvent molecule is $H_2O$.

"Solvate" means a physical association of a compound of this disclosure with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like.

The term "substituted" means substitution with specified groups other than hydrogen, or with one or more groups, moieties, or radicals which can be the same or different, with each, for example, being independently selected.

By "antisense nucleic acid", it is meant a non-enzymatic nucleic acid molecule that binds to target RNA by means of RNA-RNA or RNA-DNA or RNA-PNA (protein nucleic acid; Egholm et al., 1993 Nature 365, 566) interactions and alters the activity of the target RNA (for a review, see Stein and Cheng, 1993 Science 261, 1004 and Woolf et al., U.S. Pat. No. 5,849,902). Typically, antisense molecules are complementary to a target sequence along a single contiguous sequence of the antisense molecule. However, in certain embodiments, an antisense molecule can bind to substrate such that the substrate molecule forms a loop, and/or an antisense molecule can bind such that the antisense molecule forms a loop. Thus, the antisense molecule can be complementary to two (or even more) non-contiguous substrate sequences or two (or even more) non-contiguous sequence portions of an antisense molecule can be complementary to a target sequence or both. In addition, antisense DNA can be used to target RNA by means of DNA-RNA interactions, thereby activating RNase H, which digests the target RNA in the duplex. The antisense oligonucleotides can comprise one or more RNAse H activating region, which is capable of activating RNAse H cleavage of a target RNA. Antisense DNA can be synthesized chemically or expressed via the use of a single stranded DNA expression vector or equivalent thereof "Antisense RNA" is an RNA strand having a sequence complementary to a target gene mRNA, that can induce RNAi by binding to the target gene mRNA. "Antisense RNA" is an RNA strand having a sequence complementary to a target gene mRNA, and thought to induce RNAi by binding to the target gene mRNA. "Sense RNA" has a sequence complementary to the antisense RNA, and annealed to its complementary antisense RNA to form iNA. These antisense and sense RNAs have been conventionally synthesized with an RNA synthesizer.

"Nucleic acid" refers to deoxyribonucleotides or ribonucleotides and polymers thereof in single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2'-O-methyl ribonucleotides, peptide-nucleic acids (PNAs).

By "RNA" is meant a molecule comprising at least one ribonucleotide residue. By "ribonucleotide" is meant a nucleotide with a hydroxyl group at the 2' position of a β-D-ribo-furanose moiety. The terms include double-stranded RNA, single-stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Such alterations can include addition of non-nucleotide material, such as to the end(s) of an interfering RNA or internally, for example at one or more nucleotides of the RNA. Nucleotides in the RNA molecules of the instant invention can also comprise non-standard nucleotides, such as non-naturally occurring nucleotides or chemically synthesized nucleotides or deoxynucleotides. These altered RNAs can be referred to as analogs or analogs of naturally-occurring RNA. As used herein, the terms "ribonucleic acid" and "RNA" refer to a molecule containing at least one ribonucleotide residue, including siRNA, antisense RNA, single stranded RNA, microRNA, mRNA, noncoding RNA, and multivalent RNA. A ribonucleotide is a nucleotide with a hydroxyl group at the 2' position of a β-D-ribo-furanose moiety. These terms include double-stranded RNA, single-stranded RNA, isolated RNA such as partially purified RNA, essentially pure RNA, synthetic RNA, recombinantly produced RNA, as well as modified and altered RNA that differs from naturally occurring RNA by the addition, deletion, substitution, modification, and/or alteration of one or more nucleotides. Alterations of an RNA can include addition of non-nucleotide material, such as to the end(s) of an interfering RNA or internally, for example at one or more nucleotides of an RNA nucleotides in an RNA molecule include non-standard nucleotides, such as non-naturally occurring nucleotides or chemically synthesized nucleotides or deoxynucleotides. These altered RNAs can be referred to as analogs.

By "nucleotide" as used herein is as recognized in the art to include natural bases (standard), and modified bases well known in the art. Such bases are generally located at the 1' position of a nucleotide sugar moiety. Nucleotides generally comprise a base, sugar, and a phosphate group. The nucleotides can be unmodified or modified at the sugar, phosphate, and/or base moiety, (also referred to interchangeably as nucleotide analogs, modified nucleotides, non-natural nucleotides, non-standard nucleotides and other; see, for example, Usman and McSwiggen, supra; Eckstein, et al., International PCT Publication No. WO 92/07065; Usman, et al, International PCT Publication No. WO 93/15187; Uhlman & Peyman, supra, all are hereby incorporated by reference herein). There are several examples of modified nucleic acid bases known in the art as summarized by Limbach, et al, Nucleic Acids Res. 22:2183, 1994. Some of the non-limiting examples of base modifications that can be introduced into nucleic acid molecules include, inosine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), propyne, and others (Burgin, et al., Biochemistry 35:14090, 1996; Uhlman & Peyman, supra). By "modified bases" in this aspect is meant nucleotide bases other than adenine, guanine, cytosine, and uracil at 1' position or their equivalents.

As used herein complementary nucleotide bases are a pair of nucleotide bases that form hydrogen bonds with each other. Adenine (A) pairs with thymine (T) or with uracil (U) in RNA, and guanine (G) pairs with cytosine (C). Complementary segments or strands of nucleic acid that hybridize (join by hydrogen bonding) with each other. By "complementary" is meant that a nucleic acid can form hydrogen bond(s) with another nucleic acid sequence either by traditional Watson-Crick or by other non-traditional modes of binding.

MicroRNAs (miRNA) are single-stranded RNA molecules of about 21-23 nucleotides in length, which regulate gene expression miRNAs are encoded by genes that are transcribed from DNA but not translated into protein (non-coding RNA); instead they are processed from primary transcripts known as pri-miRNA to short stem-loop structures called pre-miRNA and finally to functional miRNA. Mature miRNA molecules are partially complementary to one or more messenger RNA (mRNA) molecules, and their main function is to downregulate gene expression As used herein the term small interfering RNA (siRNA), sometimes known as short interfering RNA or silencing RNA, is used to refer to a class of double-stranded RNA molecules, 16-40 nucleotides in length, that play a variety of roles in biology. Most notably, siRNA is involved in the RNA interference (RNAi) pathway, where it interferes with the expression of a specific gene. In addition to their role in the RNAi pathway, siRNAs also act in RNAi-related pathways, e.g., as an antiviral mechanism or in shaping the chromatin structure of a genome; the complexity of these pathways is only now being elucidated.

As used herein, the term RNAi refers to an RNA-dependent gene silencing process that is controlled by the RNA-induced silencing complex (RISC) and is initiated by short double-stranded RNA molecules in a cell, where they interact with the catalytic RISC component argonaute. When the double-stranded RNA or RNA-like iNA or siRNA is exogenous (coming from infection by a virus with an RNA genome or from transfected iNA or siRNA), the RNA or iNA is imported directly into the cytoplasm and cleaved to short fragments by the enzyme dicer. The initiating dsRNA can also be endogenous (originating in the cell), as in pre-microRNAs expressed from RNA-coding genes in the genome. The primary transcripts from such genes are first processed to form the characteristic stem-loop structure of pre-miRNA in the nucleus, then exported to the cytoplasm to be cleaved by dicer. Thus, the two dsRNA pathways, exogenous and endogenous, converge at the RISC complex. The active components of an RNA-induced silencing complex (RISC) are endonucleases called argonaute proteins, which cleave the target mRNA strand complementary to their bound siRNA or iNA. As the fragments produced by dicer are double-stranded, they could each in theory produce a functional siRNA or iNA. However, only one of the two strands, which is known as the guide strand, binds the argonaute protein and directs gene silencing. The other anti-guide strand or passenger strand is degraded during RISC activation.

The compounds of formula (1) form salts that are also within the scope of this disclosure. Reference to a compound of formula (1) herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of formula (1) contains both a basic moiety, such as, but not limited to, a pyridine or imidazole, and an acidic moiety, such as, but not limited to, a carboxylic acid, zwitterions ("inner salts") may be formed and are included within the term "salt(s)" as used herein. The salts can be pharmaceutically acceptable (i.e., non-toxic, physiologically acceptable) salts, although other salts are also useful. Salts of the compounds of the formula (1) may be formed, for example, by reacting a compound of formula (1) with an amount of acid or base, such as an equivalent amount, in a medium such as one in which the salt precipitates or in an aqueous medium followed by lyophilization.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, 2-napthalenesulfonates, nicotinates, nitrates, oxalates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates) undecanoates, and the like. Additionally, acids which are generally considered suitable for the formation of pharmaceutically useful salts from basic pharmaceutical compounds are discussed, for example, by S. Berge et al, J. Pharmaceutical Sciences (1977) 66(1)1-19; P. Gould, International J. Pharmaceutics (1986) 33 201-217; Anderson et al, The Practice of Medicinal Chemistry (1996), Academic Press, New York; and in The Orange Book (Food & Drug Administration, Washington, D.C. on their website). These disclosures are incorporated by reference herein.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine, and the like. Basic nitrogen-containing groups may be quarternized with agents such as lower alkyl halides (e.g., methyl, ethyl, propyl, and butyl chlorides, bromides, and iodides), dialkyl sulfates (e g, dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

All such acid and base salts are intended to be pharmaceutically acceptable salts within the scope of the disclosure and all acid and base salts are considered equivalent to the free forms of the corresponding compounds for purposes of the disclosure.

Compounds of formula (1) can exist in unsolvated and solvated forms, including hydrated forms. In general, the solvated forms, with pharmaceutically acceptable solvents such as water, ethanol, and the like, are equivalent to the unsolvated forms for the purposes of this disclosure.

Compounds of formula (1) and salts, solvates thereof, may exist in their tautomeric form (for example, as an amide or imino ether). All such tautomeric forms are contemplated herein as part of the present disclosure.

Also within the scope of the present disclosure are polymorphs of the compounds of this disclosure (i.e., polymorphs of the compounds of formula 1 are within the scope of this disclosure).

All stereoisomers (for example, geometric isomers, optical isomers, and the like) of the present compounds (including those of the salts, solvates, and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this disclosure. Individual stereoisomers of the compounds of this disclosure may, for example, be substantially free of other isomers, or may be admixed, for example, as racemates or with all other, or other selected, stereoisomers. The chiral centers of the compounds herein can have the S or R configuration as defined by the IUPAC 1974 Recommendations. The use of the terms "salt", "solvate", and the like, is intended to equally apply to the salt and solvate of enantiomers, stereoisomers, rotamers, tautomers, racemates, or prodrugs of the disclosed compounds.

Classes of compounds that can be used as the chemotherapeutic agent (antineoplastic agent) include: alkylating agents, antimetabolites, natural products and their derivatives, hormones and steroids (including synthetic analogs), and synthetics. Examples of compounds within these classes are given below.

Cationic Lipids

The description includes synthesis of certain cationic lipid compounds. The compounds are particularly suitable for delivering polynucleotides to cells and tissues as demonstrated in subsequent sections. The lipomacrocycle compound described herein may be used for other purposes as well as, for example, recipients and additives.

The synthetic methods for the cationic lipid compounds can be synthesized with the skills in the art. The skilled of the art will recognize other methods to produce these compounds, and to produce also the other compounds of the description.

The cationic lipid compounds may be combined with an agent to form microparticles, nanoparticles, liposomes, or micelles. The agent to be delivered by the particles, liposomes, or micelles may be in the form of a gas, liquid, or solid, and the agent may be a polynucleotide, protein, peptide, or small molecule. The lipomacrocycle compounds may be combined with other cationic lipid compounds, polymers (synthetic or natural), surfactants, cholesterol, carbohydrates, proteins, lipids, etc. to form the particles. These particles may then optionally be combined with a pharmaceutical excipient to form a pharmaceutical composition.

The present description provides novel cationic lipid compounds and drug delivery systems based on the use of such cationic lipid compounds. The system may be used in the pharmaceutical/drug delivery arts to deliver polynucleotides, proteins, small molecules, peptides, antigen, drugs, etc. to a patient, tissue, organ, or cell. These novel compounds may also be used as materials for coating, additives, excipients, materials, or bioengineering.

The cationic lipid compounds of the present description provide for several different uses in the drug delivery art. The amine-containing portion of the cationic lipid compounds may be used to complex polynucleotides, thereby enhancing the delivery of polynucleotide and preventing their degradation. The cationic lipid compounds may also be used in the formation of picoparticles, nanoparticles, microparticles, liposomes, and micelles containing the agent to be delivered. Preferably, the cationic lipid compounds are biocompatible and biodegradable, and the formed particles are also biodegradable and biocompatible and may be used to provide controlled, sustained release of the agent to be delivered. These and their corresponding particles may also be responsive to pH changes given that these are protonated at lower pH. They may also act as proton sponges in the delivery of an agent to a cell to cause endosome lysis.

In certain embodiments, the cationic lipid compounds are relatively non-cytotoxic. The cationic lipid compounds may be biocompatible and biodegradable. The cationic lipid may have $pK_a$ s in the range of approximately 5.5 to approximately 7.5, more preferably between approximately 6.0 and approximately 7.0. It may be designed to have a desired $pK_a$ between approximately 3.0 and approximately 9.0, or between approximately 5.0 and approximately 8.0. The cationic lipid compounds described herein are particularly attractive for drug delivery for several reasons: they contain amino groups for interacting with DNA, RNA, other polynucleotides, and other negatively charged agents, for buffering the pH, for causing endo-osmolysis, for protecting the agent to be delivered, they can be synthesized from commercially available starting materials; and/or they are pH responsive and can be engineered with a desired $pK_a$.

A composition containing a cationic lipid compound may be 30-70% cationic lipid compound, 0-60% cholesterol, 0-30% phospholipid and 1-10% polyethylene glycol (PEG). Preferably, the composition is 30-40% cationic lipid compound, 40-50% cholesterol, and 10-20% PEG. In other preferred embodiments, the composition is 50-75% cationic lipid compound, 20-40% cholesterol, and 5 to 10% phospholipid, and 1-10% PEG. The composition may contain 60-70% cationic lipid compound, 25-35% cholesterol, and 5-10% PEG. The composition may contain up to 90% cationic lipid compound and 2 to 15% helper lipid.

The formulation may be a lipid particle formulation, for example containing 8-30% compound, 5-30% helper lipid, and 0-20% cholesterol; 4-25% cationic lipid, 4-25% helper lipid, 2 to 25% cholesterol, 10 to 35% cholesterol-PEG, and 5% cholesterol-amine; or 2-30% cationic lipid, 2-30% helper lipid, 1 to 15% cholesterol, 2 to 35% cholesterol-PEG, and 1-20% cholesterol-amine; or up to 90% cationic lipid and 2-10% helper lipids, or even 100% cationic lipid.

Compositions and Formulations for Administration

The nucleic acid-lipid compositions of this disclosure may be administered by various routes, for example, to effect systemic delivery via intravenous, parenteral, intraperitoneal, or topical routes. In some embodiments, a siRNA may be delivered intracellularly, for example, in cells of a target tissue such as lung or liver, or in inflamed tissues. In some embodiments, this disclosure provides a method for delivery of siRNA in vivo. A nucleic acid-lipid composition may be administered intravenously, subcutaneously, or intraperitoneally to a subject. In some embodiments, the disclosure provides methods for in vivo delivery of interfering RNA to the lung of a mammalian subject.

In some embodiments, this disclosure provides a method of treating a disease or disorder in a mammalian subject. A therapeutically effective amount of a composition of this disclosure containing a nucleic, a cationic lipid, an amphiphile, a phospholipid, cholesterol, and a PEG-linked cholesterol may be administered to a subject having a disease or disorder associated with expression or overexpression of a gene that can be reduced, decreased, downregulated, or silenced by the composition.

The compositions and methods of the disclosure may be administered to subjects by a variety of mucosal administration modes, including by oral, rectal, vaginal, intranasal, intrapulmonary, or transdermal or dermal delivery, or by topical delivery to the eyes, ears, skin, or other mucosal surfaces. In some aspects of this disclosure, the mucosal tissue layer includes an epithelial cell layer. The epithelial cell can be pulmonary, tracheal, bronchial, alveolar, nasal, buccal, epidermal, or gastrointestinal. Compositions of this disclosure can be administered using conventional actuators such as mechanical spray devices, as well as pressurized, electrically activated, or other types of actuators.

Compositions of this disclosure may be administered in an aqueous solution as a nasal or pulmonary spray and may be dispensed in spray form by a variety of methods known to those skilled in the art. Pulmonary delivery of a composition of this disclosure is achieved by administering the composition in the form of drops, particles, or spray, which can be, for example, aerosolized, atomized, or nebulized. Particles of the composition, spray, or aerosol can be in either a liquid or solid form. Preferred systems for dispensing liquids as a nasal spray are disclosed in U.S. Pat. No. 4,511,069. Such formulations may be conveniently prepared by dissolving compositions according to the present disclosure in water to produce an aqueous solution, and rendering said solution sterile. The formulations may be presented in multi-dose containers, for example in the sealed dispensing system disclosed in U.S. Pat. No. 4,511,069. Other suitable nasal spray delivery systems have been described in Transdermal Systemic Medication, Y. W. Chien ed., Elsevier Publishers, New York, 1985; and in U.S. Pat. No. 4,778,810. Additional aerosol delivery forms may include, e.g., compressed air-, jet-, ultrasonic-, and piezoelectric nebulizers, which deliver the biologically active agent dissolved or suspended in a pharmaceutical solvent, e.g., water, ethanol, or mixtures thereof.

Nasal and pulmonary spray solutions of the present disclosure typically comprise the drug or drug to be delivered, optionally formulated with a surface active agent, such as a nonionic surfactant (e.g., polysorbate-80), and one or more buffers. In some embodiments of the present disclosure, the nasal spray solution further comprises a propellant. The pH of the nasal spray solution may be from about pH 6.8 to 7.2. The pharmaceutical solvents employed can also be a slightly acidic aqueous buffer of pH 4-6. Other components may be added to enhance or maintain chemical stability, including preservatives, surfactants, dispersants, or gases.

In some embodiments, this disclosure is a pharmaceutical product which includes a solution containing a composition of this disclosure and an actuator for a pulmonary, mucosal, or intranasal spray or aerosol.

A dosage form of the composition of this disclosure can be liquid, in the form of droplets or an emulsion, or in the form of an aerosol.

A dosage form of the composition of this disclosure can be solid, which can be reconstituted in a liquid prior to administration. The solid can be administered as a powder. The solid can be in the form of a capsule, tablet, or gel.

To formulate compositions for pulmonary delivery within the present disclosure, the biologically active agent can be combined with various pharmaceutically acceptable additives, as well as a base or carrier for dispersion of the active agent(s). Examples of additives include pH control agents such as arginine, sodium hydroxide, glycine, hydrochloric acid, citric acid, and mixtures thereof. Other additives include local anesthetics (e.g., benzyl alcohol), isotonizing agents (e.g., sodium chloride, mannitol, sorbitol), adsorption inhibitors (e.g., Tween 80), solubility enhancing agents (e.g., cyclodextrins and derivatives thereof), stabilizers (e.g., serum albumin), and reducing agents (e.g., glutathione). When the composition for mucosal delivery is a liquid, the tonicity of the formulation, as measured with reference to the tonicity of 0.9% (w/v) physiological saline solution taken as unity, is typically adjusted to a value at which no substantial, irreversible tissue damage will be induced in the mucosa at the site of administration. Generally, the tonicity of the solution is adjusted to a value of about ⅓ to 3, more typically ½ to 2, and most often ¾ to 1.7.

The biologically active agent may be dispersed in a base or vehicle, which may comprise a hydrophilic compound having a capacity to disperse the active agent and any desired additives. The base may be selected from a wide range of suitable carriers, including but not limited to, copolymers of polycarboxylic acids or salts thereof, carboxylic anhydrides (e.g. maleic anhydride) with other monomers (e.g., methyl(meth)acrylate, acrylic acid, etc.), hydrophilic vinyl polymers such as polyvinyl acetate, polyvinyl alcohol, polyvinylpyrrolidone, cellulose derivatives such as hydroxymethylcellulose, hydroxypropylcellulose, etc., and natural polymers such as chitosan, collagen, sodium alginate, gelatin, hyaluronic acid, and nontoxic metal salts thereof. Often, a biodegradable polymer is selected as a base or carrier, for example, polylactic acid, poly(lactic acid-glycolic acid) copolymer, polyhydroxybutyric acid, poly (hydroxybutyric acid-glycolic acid) copolymer and mixtures thereof. Alternatively or additionally, synthetic fatty acid esters such as polyglycerin fatty acid esters, sucrose fatty acid esters, etc., can be employed as carriers. Hydrophilic polymers and other carriers can be used alone or in combination, and enhanced structural integrity can be imparted to the carrier by partial crystallization, ionic bonding, cross-linking, and the like. The carrier can be provided in a variety of forms, including fluid or viscous solutions, gels, pastes, powders, microspheres, and films for direct application to the nasal mucosa. The use of a selected carrier in this context may result in promotion of absorption of the biologically active agent.

Formulations for mucosal, nasal, or pulmonary delivery may contain a hydrophilic low molecular weight compound as a base or excipient. Such hydrophilic low molecular weight compounds provide a passage medium through which a water-soluble active agent, such as a physiologically active peptide or protein, may diffuse through the base to the body surface where the active agent is absorbed. The hydrophilic low molecular weight compound optionally absorbs moisture from the mucosa or the administration atmosphere and dissolves the water-soluble active peptide. The molecular weight of the hydrophilic low molecular weight compound is generally not more than 10,000 and preferably not more than 3000. Examples of hydrophilic low molecular weight compounds include polyol compounds, such as oligo-, di- and monosaccarides including sucrose, mannitol, lactose, L-arabinose, D-erythrose, D-ribose, D-xylose, D-mannose, D-galactose, lactulose, cellobiose, gentibiose, glycerin, polyethylene glycol, and mixtures thereof. Further examples of hydrophilic low molecular weight compounds include N-methylpyrrolidone, alcohols (e.g., oligovinyl alcohol, ethanol, ethylene glycol, propylene glycol, etc.), and mixtures thereof.

The compositions of this disclosure may alternatively contain as pharmaceutically acceptable carriers substances as required to approximate physiological conditions, such as pH adjusting and buffering agents, tonicity adjusting agents, and wetting agents, for example, sodium acetate, sodium lactate, sodium chloride, potassium chloride, calcium chloride, sorbitan monolaurate, triethanolamine oleate, and mixtures thereof. For solid compositions, conventional nontoxic pharmaceutically acceptable carriers can be used which include, for example, pharmaceutical grades of mannitol, lactose, starch, magnesium stearate, sodium saccharin, talcum, cellulose, glucose, sucrose, magnesium carbonate, and the like.

In certain embodiments of the disclosure, the biologically active agent may be administered in a time release formulation, for example in a composition which includes a slow release polymer. The active agent can be prepared with carriers that will protect against rapid release, for example a controlled release vehicle such as a polymer, microencapsulated delivery system or bioadhesive gel. Prolonged delivery of the active agent, in various compositions of the disclosure can be brought about by including in the composition agents that delay absorption, for example, aluminum monosterate hydrogels and gelatin.

While this disclosure has been described in relation to certain embodiments, and many details have been set forth for purposes of illustration, it will be apparent to those skilled in the art that this disclosure includes additional embodiments, and that some of the details described herein may be varied considerably without departing from this disclosure. This disclosure includes such additional embodiments, modifications and equivalents. In particular, this disclosure includes any combination of the features, terms, or elements of the various illustrative components and examples.

EXAMPLES

Example 1

Exemplary compounds of formula (1) are provided in Table 1.

TABLE 1

| Lipid ID | Novel Lipid | MW | pKa | KD @ 0.3 mg/kg |
|---|---|---|---|---|
| ATX-001 | 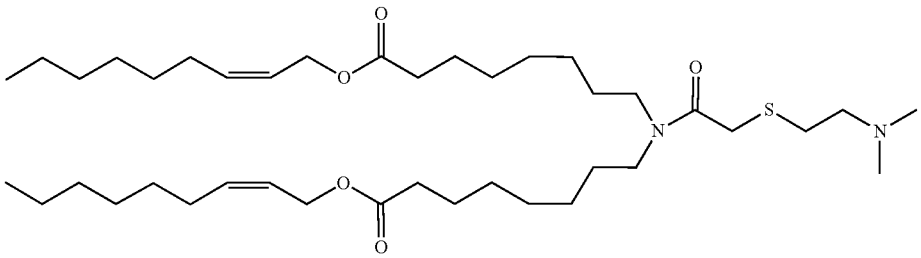 | 695.1 | 8.9 | ⁻0 |

TABLE 1-continued
| Lipid ID | Novel Lipid | MW | pKa | KD @ 0.3 mg/kg |
|---|---|---|---|---|
| ATX-002 | 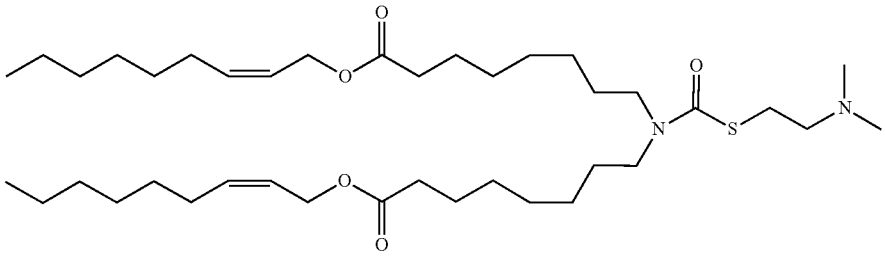 | 681 | 8.7 | 98 |
| ATX-003 | 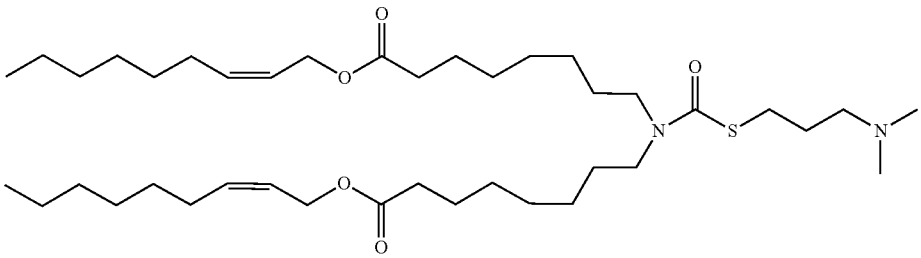 | 695.1 | 9.3 | ~0 |
| ATX-004 | 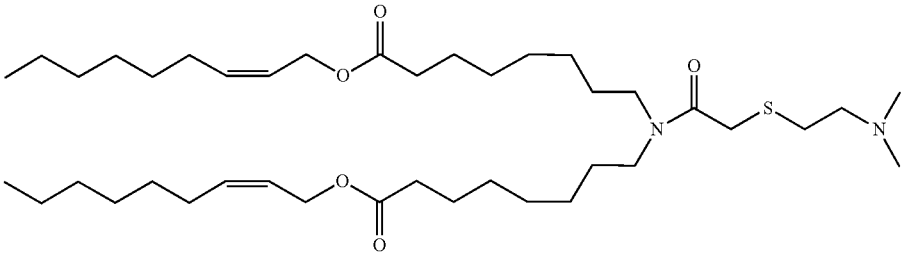 | 709.13 | 9.4 | ~0 |
| ATX-005 | 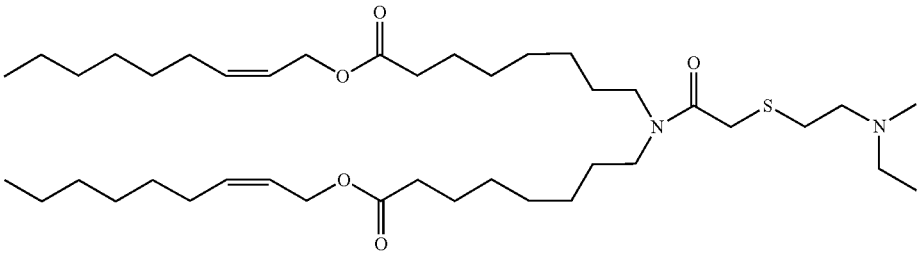 | 709.13 | 9.0 | ~0 |
| ATX-006 | 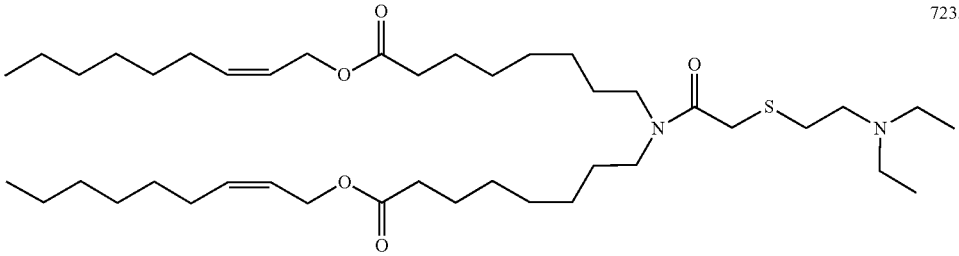 | 723.15 | 9.8 | ~0 |

TABLE 1-continued
| Lipid ID | Novel Lipid | MW | pKa | KD @ 0.3 mg/kg |
|---|---|---|---|---|
| ATX-007 | 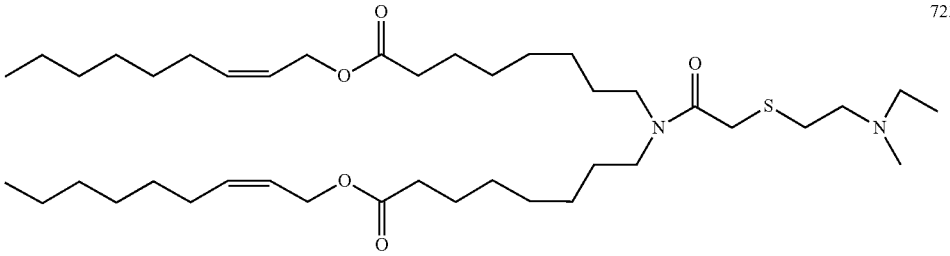 | 723.15 | 9.5 | n/a |
| ATX-008 | 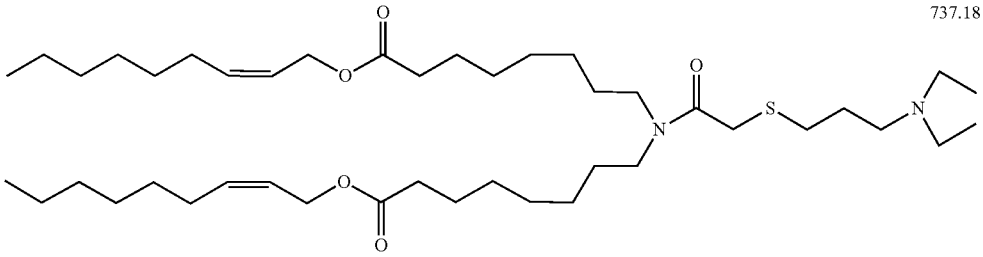 | 737.18 | 10.3 | n/a |
| ATX-009 | 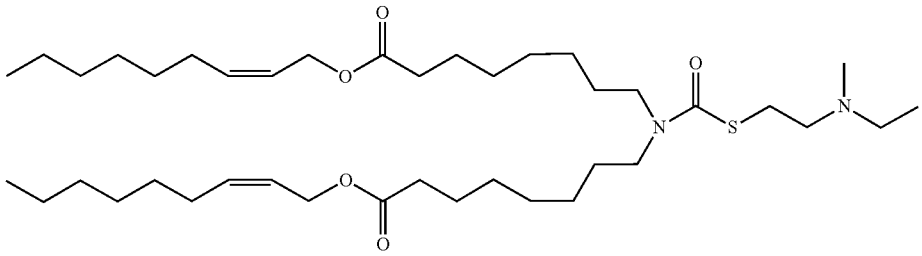 | 695.1 | 8.8 | ~0 |
| ATX-010 | 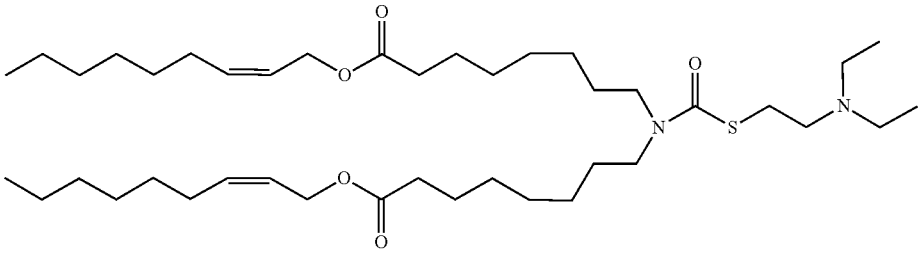 | 709.13 | 9.6 | 30 |
| ATX-011 | 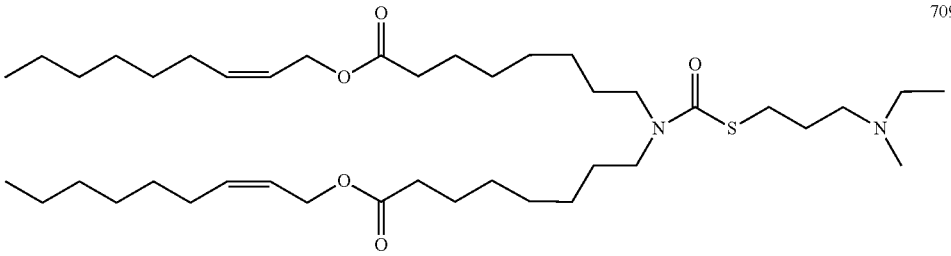 | 709.13 | 9.4 | n/a |

TABLE 1-continued
| Lipid ID | Novel Lipid | MW | pKa | KD @ 0.3 mg/kg |
|---|---|---|---|---|
| ATX-012 | 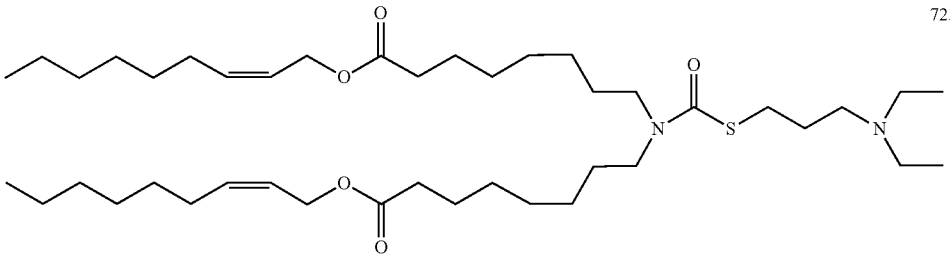 | 723.15 | 10.2 | ~0 |
| ATX-013 | 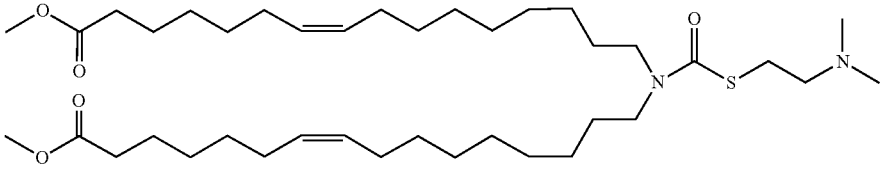 | 681.01 | | n/a |
| ATX-014 | 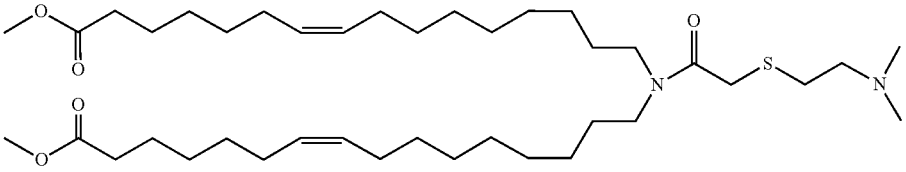 | 695.1 | | n/a |
| ATX-015 | 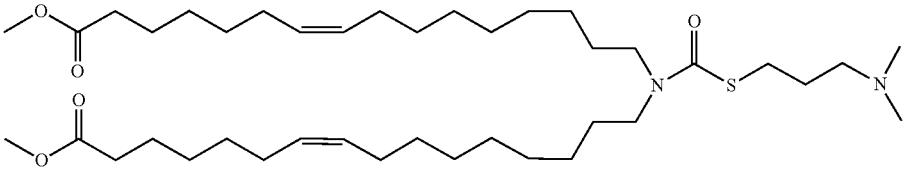 | 695.1 | | n/a |
| ATX-016 | 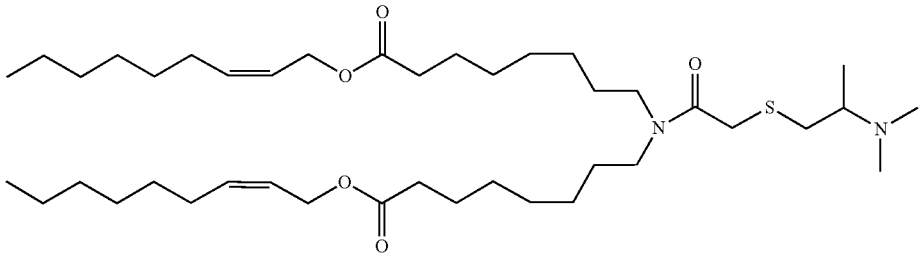 | 709.13 | | 15 |
| ATX-017 | 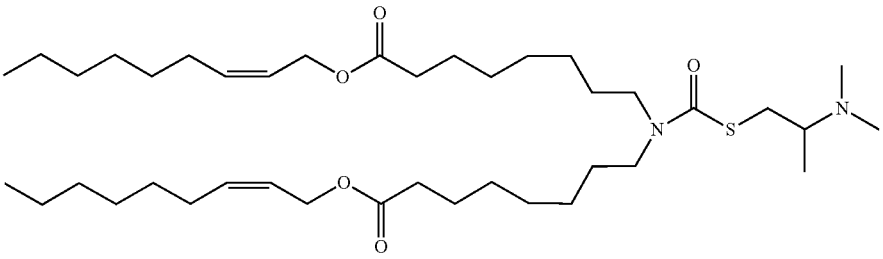 | 695.1 | | n/a |
| ATX-018 | 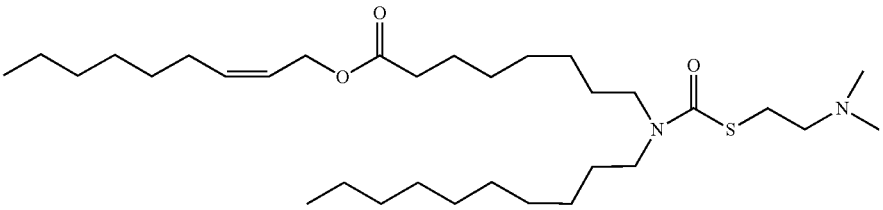 | 554.92 | | 40 (@ .05 mpk) |

TABLE 1-continued
| Lipid ID | Novel Lipid | MW | pKa | KD @ 0.3 mg/kg |
|---|---|---|---|---|
| ATX-019 | 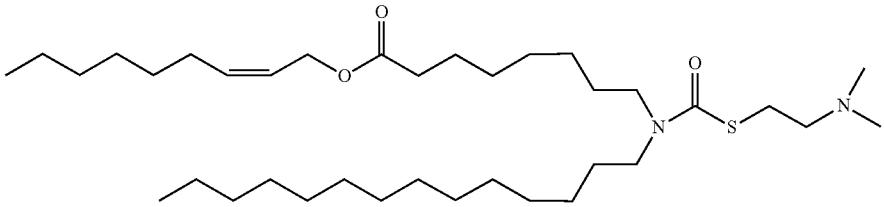 | 611.03 | | 30 (@ .05 mpk) |
| ATX-020 | 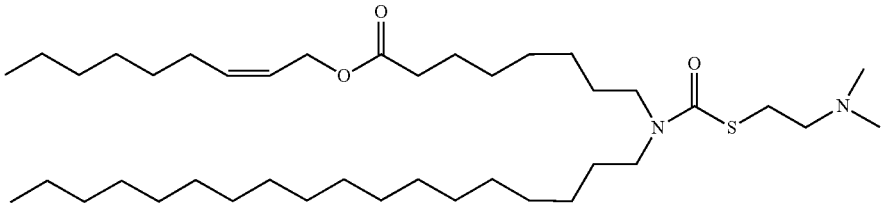 | 667.13 | | 40 (@ .05 mpk) |
| ATX-021 | 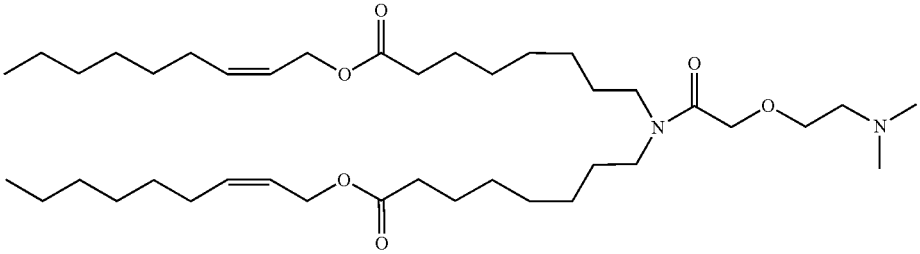 | 679.04 | | n/a |
| ATX-022 | 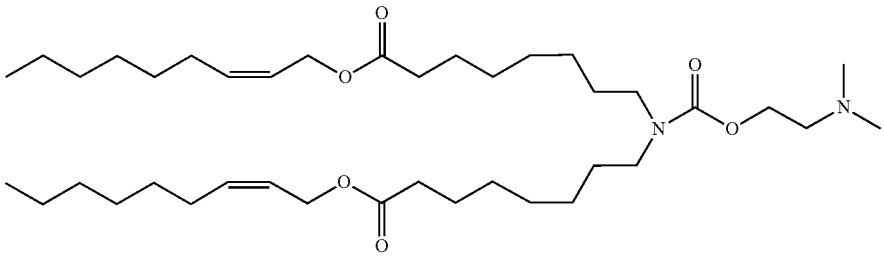 | 665.01 | | n/a |
| ATX-023 | 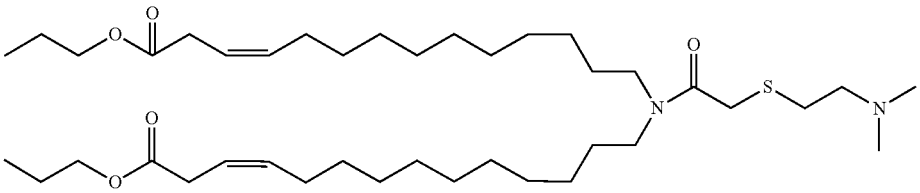 | 695.1 | | n/a |
| ATX-024 | 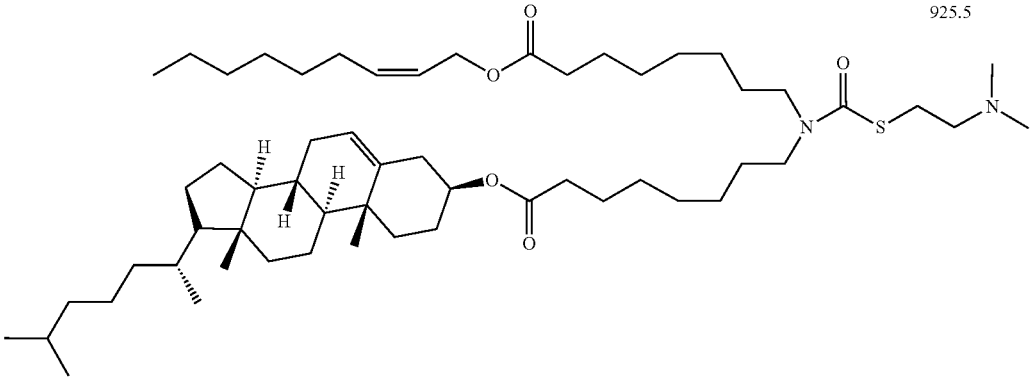 | 925.5 | | 0 |

TABLE 1-continued
| Lipid ID | Novel Lipid | MW | pKa | KD @ 0.3 mg/kg |
|---|---|---|---|---|
| ATX-025 | 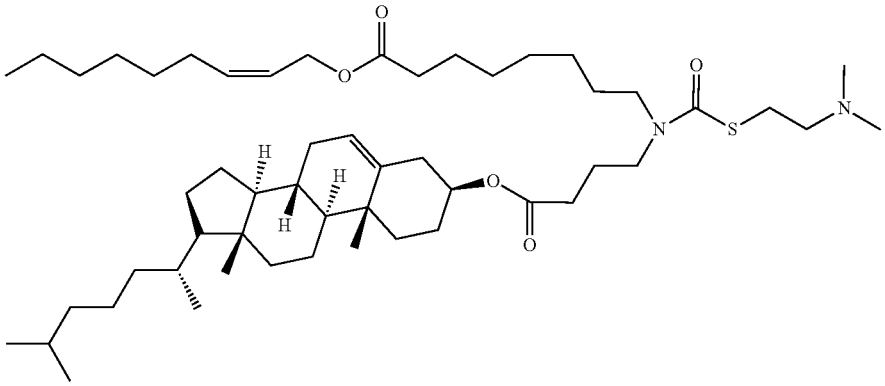 | 869.39 | | 15 |
| ATX-026 | 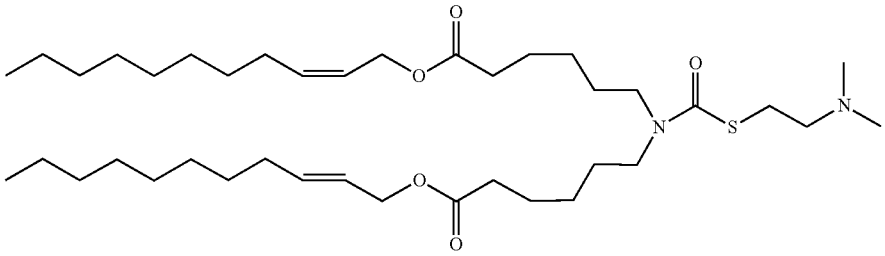 | 681.07 | | n/a |
| ATX-027 | 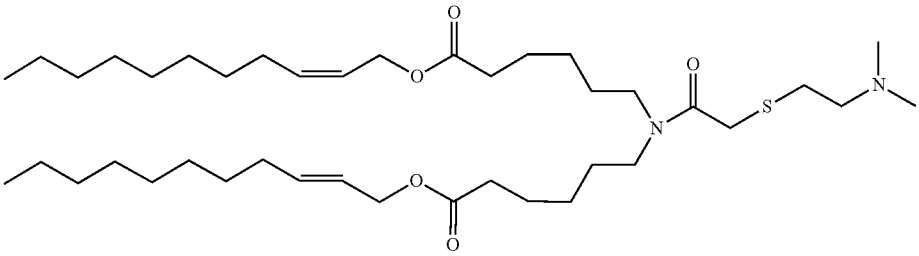 | 695.1 | | n/a |
| ATX-028 | 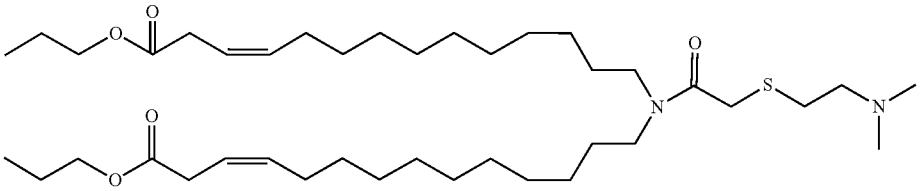 | 681.07 | | n/a |
| ATX-029 | 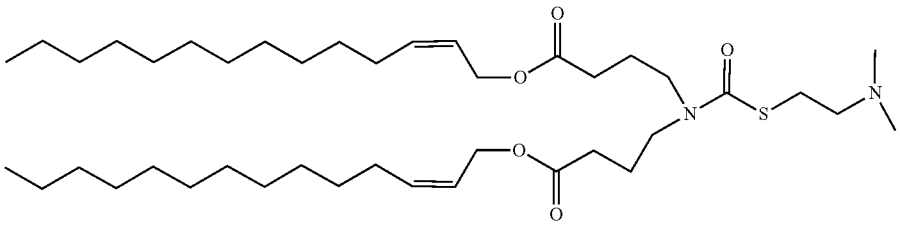 | 681.1 | | n/a |

TABLE 1-continued

| Lipid ID | Novel Lipid | MW | pKa | KD @ 0.3 mg/kg |
|---|---|---|---|---|
| ATX-030 | 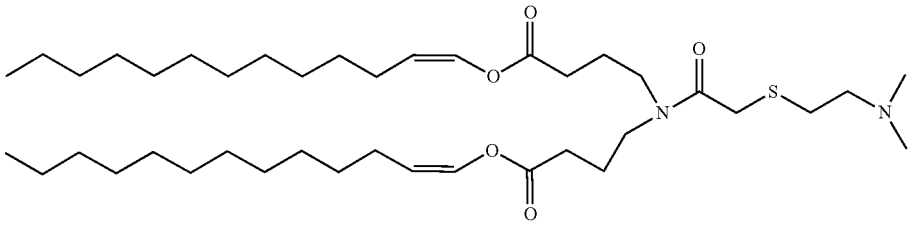 | 695.1 | | n/a |
| ATX-031 | 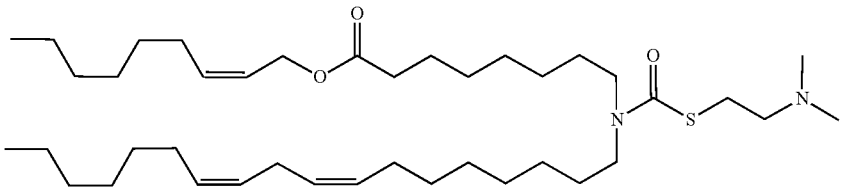 | 663.1 | | n/a |
| ATX-032 | 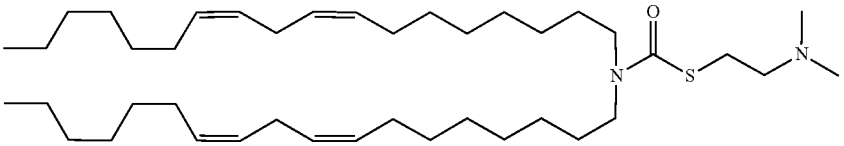 | 645.13 | | n/a |

Table 1 shows the name and structure of each compound, its molecular weight, its pKa, and its knockdown bioactivity (KD) in an assay described below in Example 19.

Example 2

Synthesis of Methyl 8-Bromooctanoate

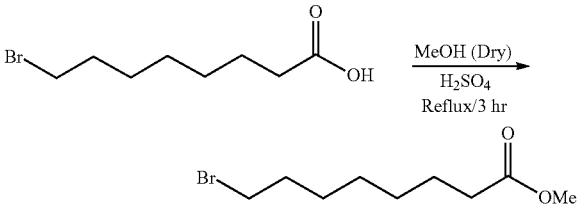

| S. No. | Chemicals/Reagents and solvents | M.Wt. | Moles | Eq. | Wt. |
|---|---|---|---|---|---|
| 1 | 8-Bromooctanoic acid | 223 | 269.05 | 1 | 60 gm. |
| 2 | Dry MeOH | | | | 400 ml |
| 3 | Con $H_2SO_4$ | | | | 10 drop |

Under N2 atmosphere, 8-bromooctanoic acid was dissolved in dry methanol. Concentrated $H_2SO_4$ was added drop-wise and the reaction mixture was stirred under reflux for three hours.

The reaction was monitored by thin layer chromatography until completed. Solvent was completely removed under vacuum. The reaction mixture was diluted with ethyl acetate and washed with water. The water layer was re-extracted with ethyl acetate. The total organic layer was washed with a saturated $NaHCO_3$ solution. The organic layer was washed again with water and finally washed with brine. The product was dried over anhydrous $Na_2SO_4$ and concentrated.

Example 3

Synthesis of dimethyl 8,8'-(benzanediyl)dioctanoate

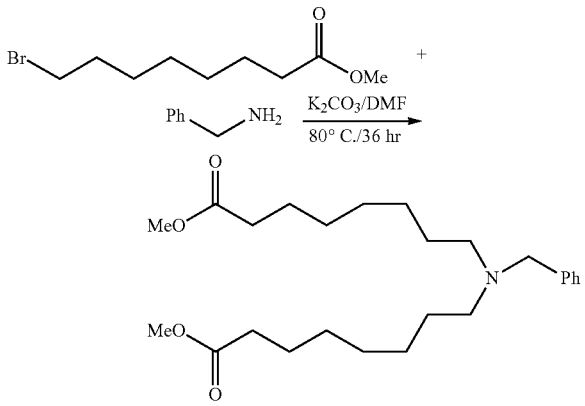

| S. No. | Chemicals/Reagents and solvents | M.Wt. | Moles | Eq. | Wt. |
|---|---|---|---|---|---|
| 1 | Benzyl amine | 107 | 126.54 | 1 | 13.54 |
| 2 | Methyl 8-bromooctanoate | 237 | 253.08 | 2 | 60 g |
| 3 | Dry $K_2CO_3$ | 138 | 759.25 | 6 | 104.7 |
| 4 | Dry DMF | | | | 500 ml |

Dry $K_2CO_3$ was taken and added to dry dimethylformamide under $N_2$. Benzyl amine in dimethylformamide was slowly added. Methyl 8-bromooctanoate dissolved in dimethylformamide was then added at room temperature. The reaction mixture was heated to 80° C. and the reaction was maintained for 36 hours with stirring.

The reaction was monitored by thin layer chromatography until completed. The reaction product was cooled to room temperature and water was added. The compound was extracted with ethyl acetate. The water layer was re-extracted with ethyl acetate. The total organic layer was washed with water and finally with brine solution. The product was dried over anhydrous $Na_2SO_4$ and concentrated.

The reaction product was purified by silica gel column chromatography in 3% methanol in chloroform. 44 gm of pure product was recovered.

Using TLC system of 10% methanol in chloroform, the product migrated with a Rf: 0.8, visualizing by charring in ninhydrine. The overall yield was 82%. The compound was a light brown liquid. The structure was confirmed by 1H-NMR.

Example 4

Synthesis of Dimethyl 8,8'-Azanediyldioctanoate

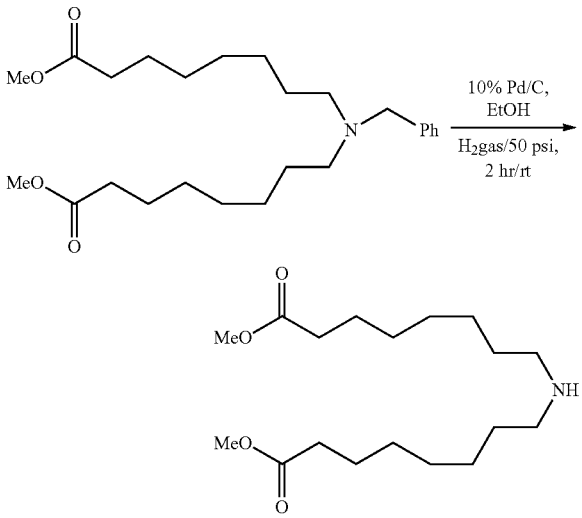

| S. No. | Chemicals/Reagents and solvents | M.Wt. | mmoles | Eq. | Wt. |
|---|---|---|---|---|---|
| 1 | Dimethyl 8,8'-(benzanediyl) dioctanoate | 419.60 | 8.34 | 1 | 3.5 gm |
| 2 | 10% Pd/C | | 20% wt | | 700 mg |
| 3 | Ethanol | | | | 90 ml |

Dimethyl 8,8'-(benzanediyl)dioctanoate was transferred to hydrogenation glass vessel, and ethanol was added followed by 10% Pd/C. The reaction mixture was shaken in a Parr-shaker apparatus under 50 pounds per square inch [psi] $H_2$ atmosphere pressure for two hours at room temperature.

The reaction product was filtered through celite and washed with hot ethyl acetate. The filtrate was concentrated under vacuum.

Example 5

Synthesis of Dimethyl 8,8'-((Tertbutoxycarbonyl)Azanedil) Dioctanoate

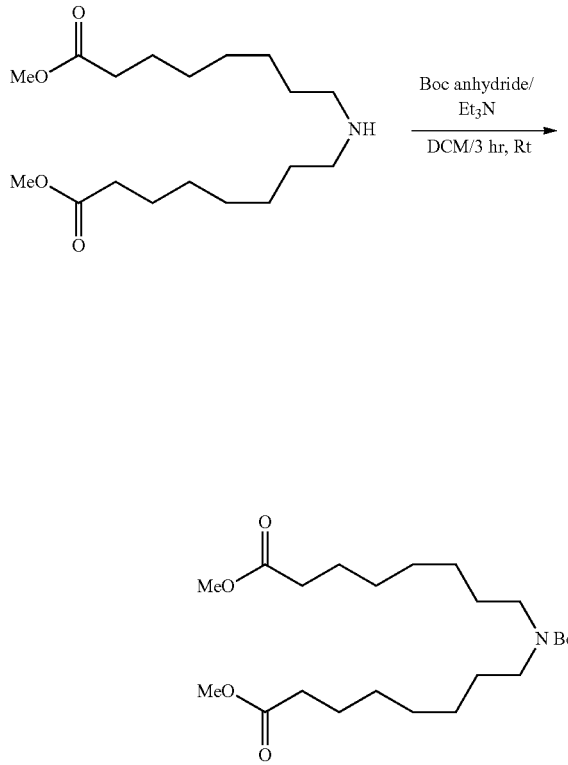

| S. No | Chemicals/reagents/solvents | Mw | Mole's | Eq | wt |
|---|---|---|---|---|---|
| 1 | Dimethyl 8,8'-azanediyl-dioctanoate | 329 | 0.0972 | 1 | 32 gm |
| 2 | Boc anhydride | 218 | 0.145 | 1.5 | 31.3 gm |
| 3 | $Et_3N$ (Dry) | 101 | 0.389 | 4 | 9 gm |
| 4 | DCM(Dry) | | | | 700 ml |

Dimethyl 8,8'-azanediyldioctanoate was transferred to DCM and $Et_3N$ to the reaction mass and cooled to 0° C. Boc anhydride diluted in DCM was added drop to the above reaction. After the addition was completed, the reaction mixture was stirred at room temperature for three hours.

The reaction was quenched with water and the DCM layer was separated. The water phase was re-extracted with DCM and the combined DCM layers were washed with brine solution and dried with $Na_2SO_4$. After concentration, 40 gm of crude compound was collected.

Crude reaction product was purified by column chromatography using 0-12% ethyl acetate in hexane. The yield recovered was 48%. A single product migrated by thin layer chromatography in 20% ethyl acetate in hexane with an Rf of 0.5, charring with ninhydrine.

Example 6

Synthesis of 8,8'-((Tertbutoxycarbonyl)Azanediyl) Dioctanoic Acid

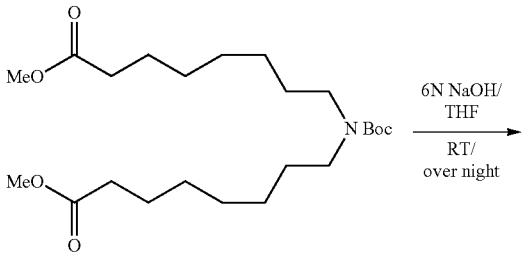

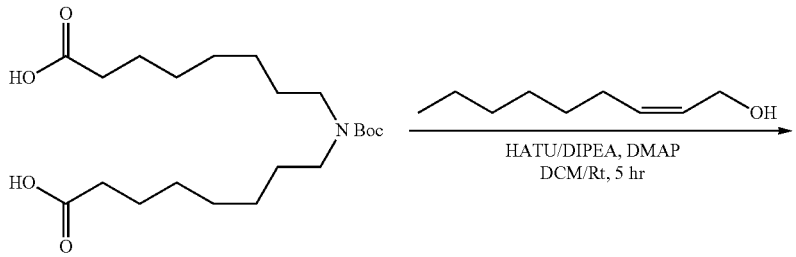

7

-continued

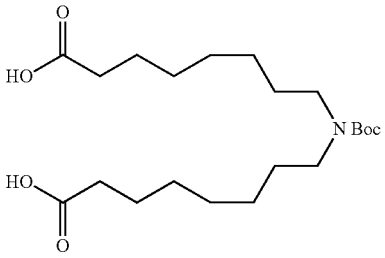

| S. No | Chemicals/reagents/solvents | Mw | Mole's | Eq | wt |
|---|---|---|---|---|---|
| 1 | Dimethyl 8,8' ((tertbutoxycarbonyl)azanediyl) dioctanoate | 429 | 0.0489 | 1 | 21 gm |
| 2 | 6N NaOH (aq.) | | | | 175 ml |
| 3 | Dry THF | | | | 200 ml |

Dimethyl 8,8'-((tertbutoxycarbonyl)azanedil) dioctanoate was transferred to THF. A 6N sodium hydroxide solution was added at room temperature. The reaction was maintained with stirring overnight at room temperature.

Reaction mass was evaporated under vacuum at 25° C. to remove THF. The reaction product was acidified with 5N HCl. Ethyl acetate was added to the aqueous layer. The separated organic layer was washed with water and the water layer was re-extracted with ethyl acetate. The combined organic layers were washed with brine solution and dried over anhydrous $Na_2SO_4$. Concentration of the solution gave 18 gm of crude mass.

Example 7

Synthesis of di((Z)-non-2-en-1-yl) 8,8'((tertbutoxycarbonyl)azanediyl)

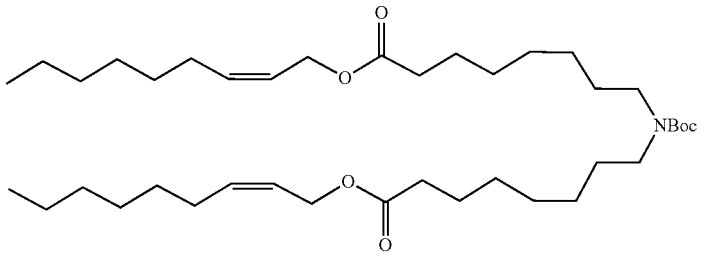

| S. No | Chemicals/reagents/ solvents | Mw | Mole's | Eq | wt |
|---|---|---|---|---|---|
| 1 | 8,8'-((tertbutoxycarbonyl) azanediyl) dioctanoic acid | 549.5 | 0.03275 | 1 | 18 gm |
| 2 | Cis-2-nonene-1-ol | 142.24 | 0.065514 | 2 | 9.31 gm |
| 3 | HATU | 380.23 | 0.06878 | 2.1 | 26.15 gm |
| 4 | Di-Isopropyl ethyl amine | 129.25 | 0.1146 | 3.5 | 14.81 gm |
| 5 | DMAP | 122.17 | 0.003275 | 0.1 | 400 mg |
| 6 | Dry-DCM | | | | 150 ml |

8,8'-((tertbutoxycarbonyl)azanediyl) dioctanoic acid was dissolved in dry DCM. HATU was added to this solution. Di-isopropyl ethyl amine was added slowly to the reaction mixture at room temperature. The internal temp rose to 40° C. and a pale yellow color solution was formed. DMAP was added to the reaction mixture followed by cis-2-nonene-1-ol solution in dry DCM. The reaction changed to brown color. The reaction was stirred for five hours at room temperature.

The reaction was checked by thin layer chromatography under completion. Water was added to the reaction product, which was extracted with DCM. The DCM layer was washed with water followed by brine solution. The organic layer was dried over anhydrous $Na_2SO_4$ and concentrated to obtain 35 gm of crude compound.

Example 8

Synthesis of ATX-001

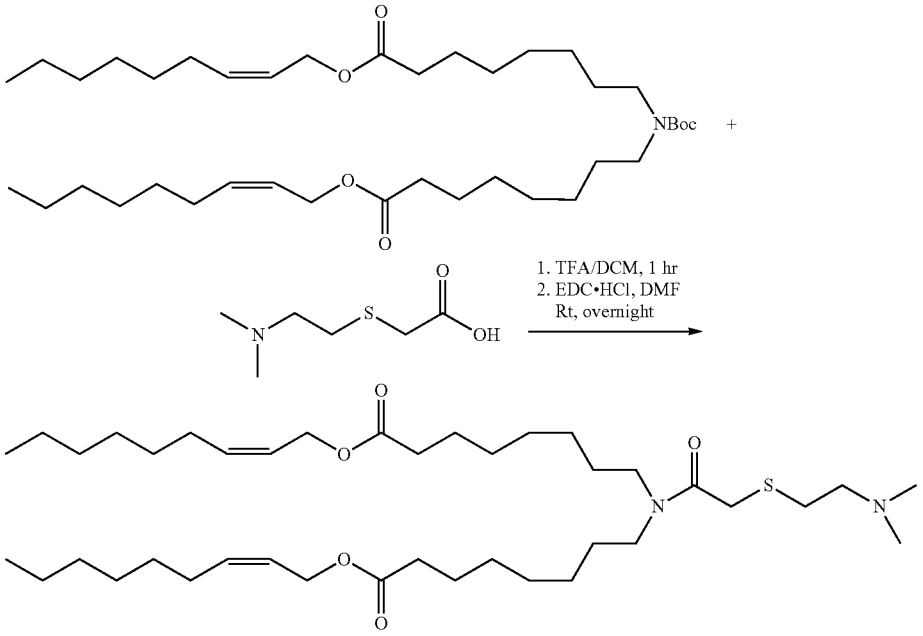

ATX-2

Di((Z)-non-2-en-1-yl) 8,8'((tertbutoxycarbonyl) azanediyl) dioctanoate (0.023 mol, 15 g) was dissolved in dry dichloromethane (DCM) (200 ml). Trifluoroacetic acid (TFA) was added at 0° C. to initiate a reaction. The reaction temperature was slowly allowed to warm to room temperature over for 30 minutes with stirring. Thin layer chromatography showed that the reaction was completed. The reaction product was concentrated under vacuum at 40° C. and the crude residue was diluted with DCM, and washed with a 10% $NaHCO_3$ solution. The aqueous layer was re-extracted with DCM, and the combined organic layers were washed with brine solution, dried over $Na_2SO_4$ and concentrated. The collected crude product (12 grams) was dissolved in dry DCM (85 ml) under nitrogen gas. Triphosgene were added and the reaction mixture was cooled to 0° C., and $Et_3N$ was added drop wise. The reaction mixture was stirred overnight at room temperature. Thin layer chromatography showed that the reaction was completed. DCM solvent was removed from the reaction mass by distillation under $N_2$. The reaction product was cooled to 0° C., diluted with DCM (50 ml), and 2-((2-(dimethylamino)ethyl)thio) acetic acid (0.039 mol, 6.4 g) and carbodiimide (EDC HCl) (0.054 mol, 10.4 g). The reaction mixture was then stirred overnight at room temperature. Thin layer chromatography showed that the reaction was completed. The reaction product was diluted with 0.3M HCl solution (75 ml), and the organic layer was separated. The aqueous layer was re-extracted with DCM, and the combined organic layers were washed with 10% $K_2CO_3$ aqueous solution (75 ml) and dried over anhydrous $Na_2SO_4$. Concentration of the solvent gave a crude mass of 10 gram. The crude compound was purified by silica gel column (100-200 mesh) using 3% MeOH/DCM. The yield was 10.5 g (68%).

Example 9

Synthesis of ATX-002

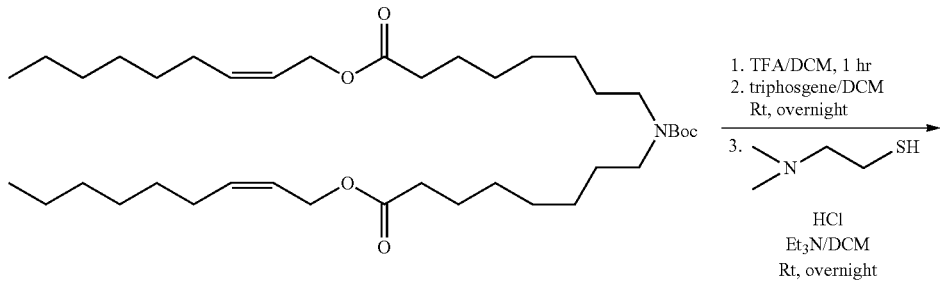

-continued

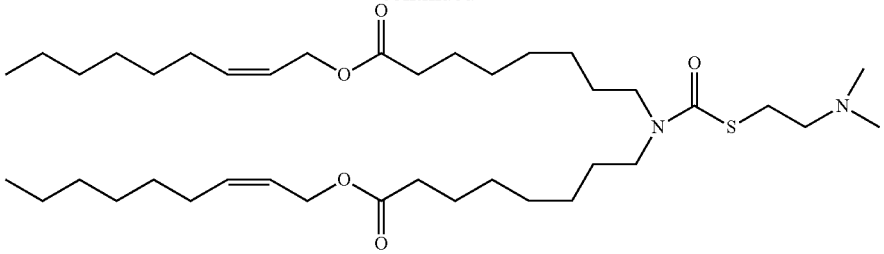

ATX-2

Di((Z)-non-2-en-1-yl) 8,8'((tertbutoxycarbonyl) azanediyl) dioctanoate (13.85 mmol, 9 grams) was dissolved in dry DCM (150 ml). TFA was added at 0° C. to initiate a reaction. The reaction temperature was slowly allowed to warm to room temperature over for 30 minutes with stirring. Thin layer chromatography showed that the reaction was completed. The reaction product was concentrated under vacuum at 40° C. and the crude residue was diluted with DCM, and washed with a 10% $NaHCO_3$ solution. The aqueous layer was re-extracted with DCM, and the combined organic layers were washed with brine solution, dried over $Na_2SO_4$ and concentrated. The collected crude product was dissolved in dry DCM (85 ml) under nitrogen gas. Triphosgene were added and the reaction mixture was cooled to 0° C., and $Et_3N$ was added drop wise. The reaction mixture was stirred overnight at room temperature. Thin layer chromatography showed that the reaction was completed. DCM solvent was removed from the reaction mass by distillation under $N_2$. The reaction product was cooled to 0° C., diluted with DCM (50 ml), and 2-(dimethylamino) ethanethiol HCl (0.063 mol, 8.3 g) was added, followed by $Et_3N$ (dry). The reaction mixture was then stirred overnight at room temperature. Thin layer chromatography showed that the reaction was completed. The reaction product was diluted with 0.3M HCl solution (75 ml), and the organic layer was separated. The aqueous layer was re-extracted with DCM, and the combined organic layers were washed with 10% $K_2CO_3$ aqueous solution (75 ml) and dried over anhydrous $Na_2SO_4$. Concentration of the solvent gave a crude mass of 10 gram. The crude compound was purified by silica gel column (100-200 mesh) using 3% MeOH/DCM. The yield was 3.1 gram.

Example 10

Synthesis of ATX-003

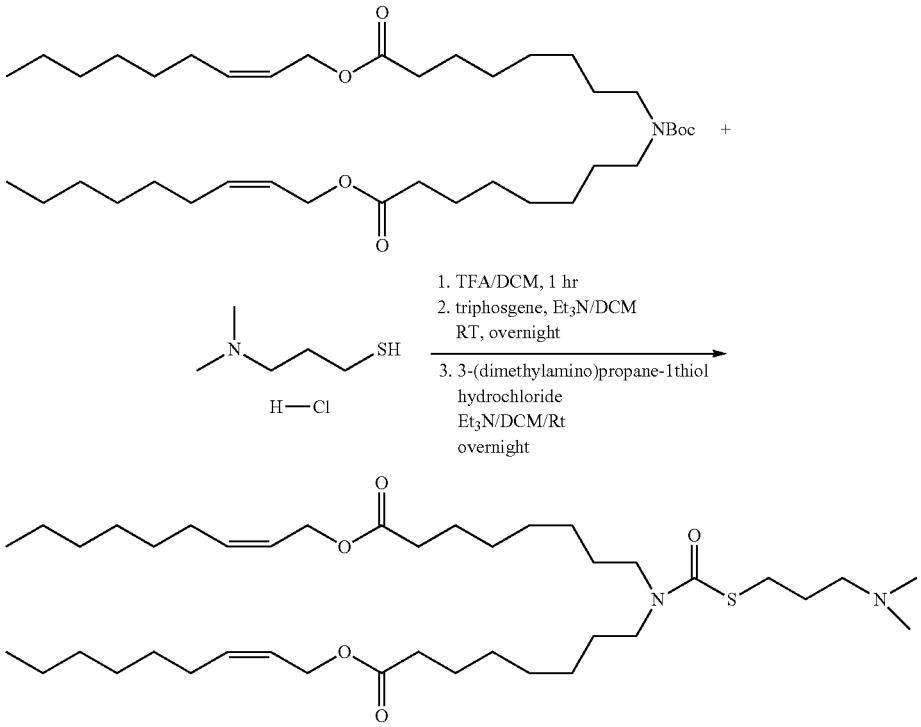

ATX-3

Di((Z)-non-2-en-1-yl) 8,8'((tertbutoxycarbonyl) azanediyl) dioctanoate (0.00337 mol, 2.2 g) was dissolved in dry DCM (20 ml). TFA was added at 0° C. to initiate a reaction. The reaction temperature was slowly allowed to warm to room temperature over for 30 minutes with stirring. Thin layer chromatography showed that the reaction was completed. The reaction product was concentrated under vacuum at 40° C. and the crude residue was diluted with DCM, and washed with a 10% $NaHCO_3$ solution. The aqueous layer was re-extracted with DCM, and the combined organic layers were washed with brine solution, dried over $Na_2SO_4$ and concentrated under reduced pressure. The collected crude product was dissolved in dry DCM (10 ml) under nitrogen gas. Triphosgene (0.0182 mol, 5.4 g) was added and the reaction mixture was cooled to 0° C., and $Et_3N$ was added drop wise. The reaction mixture was stirred overnight at room temperature. Thin layer chromatography showed that the reaction was completed. DCM solvent was removed from the reaction mass by distillation under $N_2$. The reaction product was cooled to 0° C., diluted with DCM (15 ml), and 2-(dimethylamino)propanethiol HCl (0.0182 mol, 2.82 g) was added, followed by $Et_3N$ (dry). The reaction mixture was then stirred overnight at room temperature. Thin layer chromatography showed that the reaction was completed. The reaction product was diluted with 0.3 M HCl aqueous solution (20 ml), and the organic layer was separated. The aqueous layer was re-extracted with DCM, and the combined organic layers were washed with 10% $K_2CO_3$ aqueous solution (50 ml) and dried over anhydrous $Na_2SO_4$. Concentration of the solvent gave a crude mass of 5 gram. The crude compound was purified by silica gel column (100-200 mesh) using 3% MeOH/DCM. The yield was 0.9 gram.

Example 11

Synthesis of ATX-004

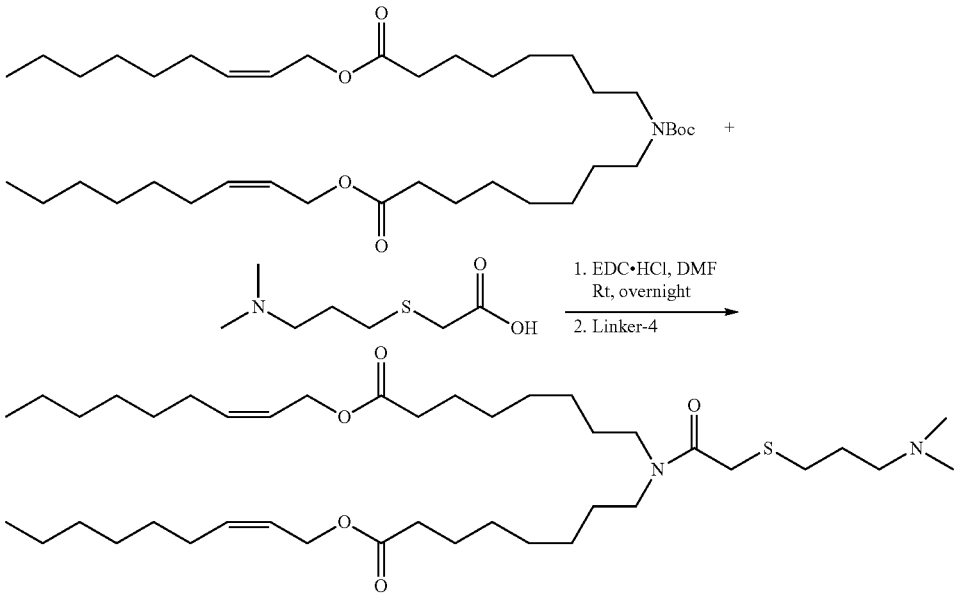

ATX-4

Di((Z)-non-2-en-1-yl) 8,8'((tertbutoxycarbonyl) azanediyl) dioctanoate (0.023 mol, 15 g) was dissolved in DCM (200 ml). TFA was added at 0° C. to initiate a reaction. The reaction temperature was slowly allowed to warm to room temperature over for 30 minutes with stirring. Thin layer chromatography showed that the reaction was completed. The reaction product was concentrated under vacuum at 40° C. and the crude residue was diluted with DCM, and washed with a 10% $NaHCO_3$ solution. The aqueous layer was re-extracted with DCM, and the combined organic layers were washed with brine solution, dried over $Na_2SO_4$ and concentrated. The collected crude product, di((Z)-non-2-en-1-yl)8,8'-azanediyldioctanoate (5.853 mmol, 3.2 g) was dissolved in dry dimethyl formamide (DMF) under nitrogen, and 2-((3-(dimethylamino)propyl) thio)acetic acid (10.48 mmol, 1.85 g) and EDC HCl (14.56 mmol, 2.78 g) was added. The reaction mixture was stirred for overnight at room temperature. The reaction was quenched with water (30 ml) and diluted with DCM (30 ml), and the organic layer was separated. The aqueous layer was re-extracted with DCM, and the combined organic layers were washed with 10% $K_2CO_3$ aqueous solution and dried over anhydrous $Na_2SO_4$. The crude compound was purified by silica gel column (100-200 mesh) using 3% MeOH/DCM. The yield was 1 gram (24.2%).

Example 12

Synthesis of ATX-005

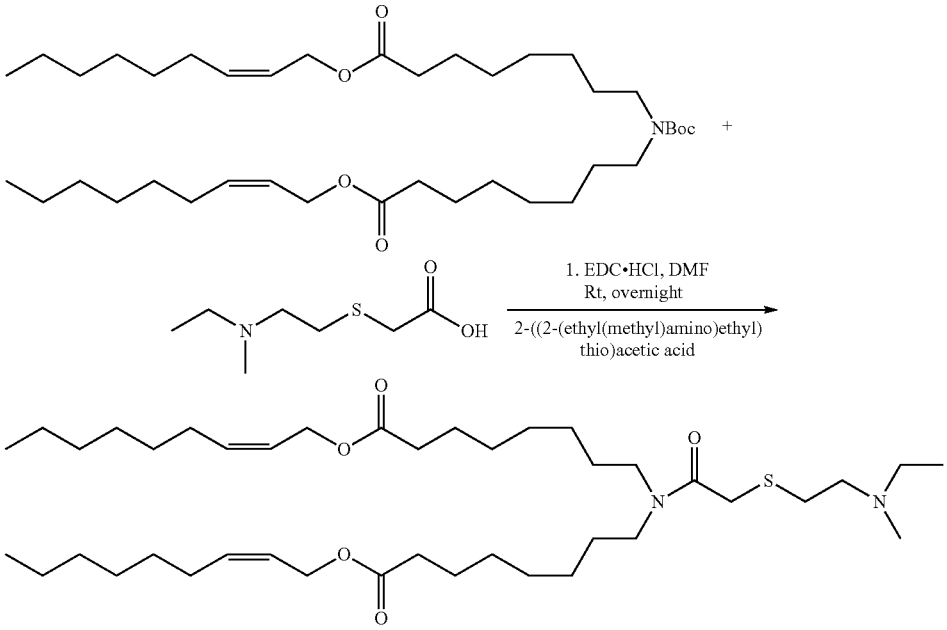

ATX-5

Di((Z)-non-2-en-1-yl) 8,8'((tertbutoxycarbonyl) azanediyl) dioctanoate (0.023 mol, 15 g) was dissolved in dry DCM (200 ml). TFA was added at 0° C. to initiate a reaction. The reaction temperature was slowly allowed to warm to room temperature over for 30 minutes with stirring. Thin layer chromatography showed that the reaction was completed. The reaction product was concentrated under vacuum at 40° C. and the crude residue was diluted with DCM, and washed with a 10% $NaHCO_3$ solution. The aqueous layer was re-extracted with DCM, and the combined organic layers were washed with brine solution, dried over $Na_2SO_4$ and concentrated. Crude reaction product, di((Z)-non-2-en-1-yl)8,8'-azanediyldioctanoate (5.853 mmol, 3.2 g) was dissolved in DMF under nitrogen gas. 2-((3-(dimethylamino)propyl)thio)acetic acid (10.48 mmol, 1.85 g) and EDC HCl (14.56 mmol, 2.78 g) were added and the reaction mixture was stirred overnight at room temperature. Thin layer chromatography showed that the reaction was completed. The reaction product was quenched with water (30 ml) and diluted with DCM (30 ml). The aqueous layer was re-extracted with DCM, and the combined organic layers were washed with 10% $K_2CO_3$ aqueous solution (75 ml) and dried over anhydrous $Na_2SO_4$. Concentration of the solvent gave a crude mass of 5 gram. Crude compound was purified by silica gel column (100-200 mesh) using 3% MeOH/DCM. The yield was 1 gram (24.2%).

Example 13

Synthesis of ATX-006

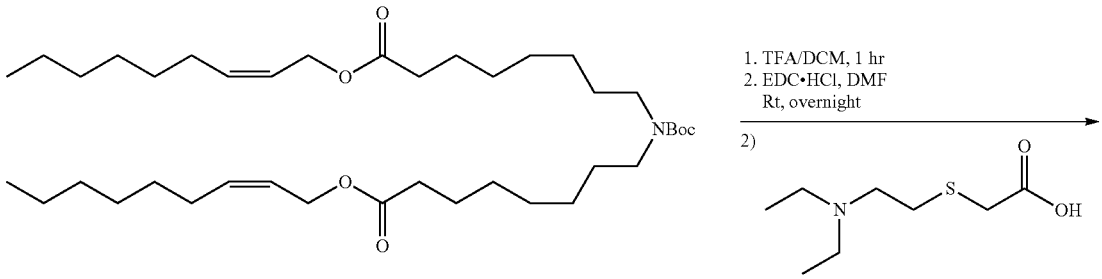

2-((2-(diethylamino)ethyl)thio)acetic acid

-continued

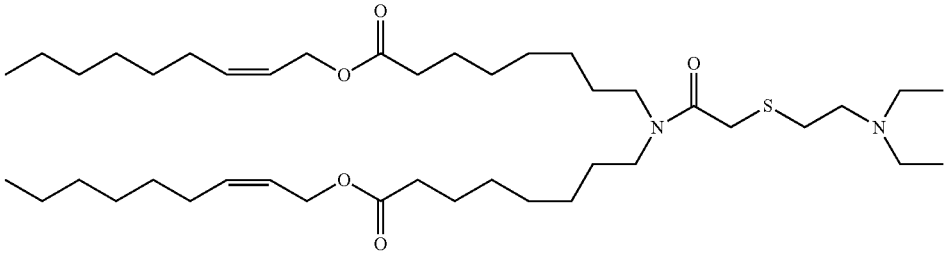

ATX-6

Di((Z)-non-2-en-1-yl) 8,8'((tertbutoxycarbonyl) azanediyl) dioctanoate was dissolved in dry DCM (150 ml). TFA was added at 0° C. to initiate a reaction. The reaction temperature was slowly allowed to warm to room temperature over for 30 minutes with stirring. Thin layer chromatography showed that the reaction was completed. The reaction product was concentrated under vacuum at 40° C. and the crude residue was diluted with DCM, and washed with a 10% $NaHCO_3$ solution. The aqueous layer was re-extracted with DCM, and the combined organic layers were washed with brine solution, dried over $Na_2SO_4$ and concentrated. The collected crude product was dissolved in dry DCM (85 ml) under nitrogen gas. Triphosgene were added and the reaction mixture was cooled to 0° C., and $Et_3N$ was added drop wise. The reaction mixture was stirred overnight at room temperature. Thin layer chromatography showed that the reaction was completed. The crude reaction produce was dissolved in dry DMF under nitrogen atmosphere, and 2-((2-(diethylamino)ethyl)thio)acetic acid (3.93 mmol, 751 mg) and EDC HCl (5.45 mmol, 1.0 g) were added. The reaction mixture was stirred for overnight at room temperature. The reaction was quenched with water (3 ml) and excess DMF was removed under vacuum at 25° C. The reaction product was diluted with water and aqueous layer was extracted thrice with DCM (20 ml). The combined organic layers were washed with brine solution and dried over anhydrous $Na_2SO_4$. Concentration of the solvent gave a crude mass of 2 gram. After purification by silica gel column (100-200 mesh) using 3% MeOH/DCM., the yield was 1.2 grams (76%).

Example 14

Synthesis of ATX-009

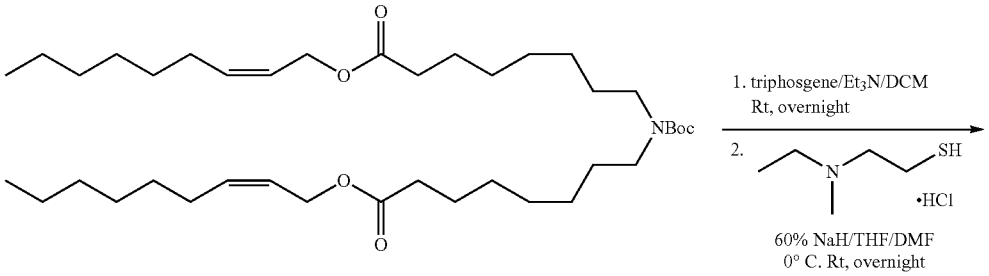

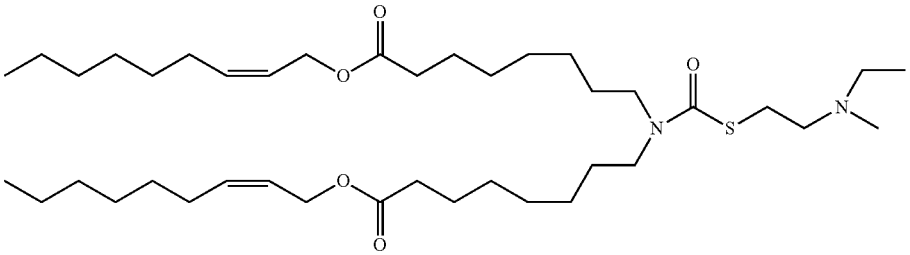

ATX-9

Di((Z)-non-2-en-1-yl) 8,8'((tertbutoxycarbonyl) azanediyl) dioctanoate (13.85 mmol, 9 grams) was dissolved in dry DCM (20 ml). TFA was added at 0° C. to initiate a reaction. The reaction temperature was slowly allowed to warm to room temperature over for 30 minutes with stirring. Thin layer chromatography showed that the reaction was completed. The reaction product was concentrated under vacuum at 40° C. and the crude residue was diluted with DCM, and washed with a 10% $NaHCO_3$ solution. The aqueous layer was re-extracted with DCM, and the combined organic layers were washed with brine solution, dried over $Na_2SO_4$ and concentrated. Di((Z)-non-2-en-1-yl)8,8'-azanediyldioctanoate (0.909 mmol, 500 mg) was dissolved in dry DCM (20 ml) under nitrogen atmosphere. Triphosgene were added and the reaction mixture was cooled to 0° C., and $Et_3N$ was added drop wise. The reaction mixture was stirred overnight at room temperature. Thin layer chromatography showed that the reaction was completed. DCM solvent was removed from the reaction mass by distillation under nitrogen atmosphere. 2-(ethyl(methyl)amino)ethane-1-thiol hydrochloride (4.575 mmol, 715 mg) was dissolved in DMF (7 ml) and tetrahydrofuran (THF) (5 ml), and was added drop wise to the sodium hydride suspension in THF at 0° C. The reaction mixture was then stirred overnight at room temperature. Thin layer chromatography showed that the reaction was completed. The reaction product was diluted with ethyl acetate and cold water. The reaction was neutralized with 5% HCl (9 ml), and the organic layer was separated. The aqueous layer was re-extracted with ethyl acetate (EtOAc) (20 ml), washed in cold water and brine, and the combined organic layers were washed dried over anhydrous $Na_2SO_4$. Concentration of the solvent gave 1 gram or crude product. The compound was purified by silica gel column (100-200 mesh) using 3% MeOH/DCM to yield 100 mg.

Example 15

Synthesis of ATX-010

Di((Z)-non-2-en-1-yl) 8,8'((tertbutoxycarbonyl) azanediyl) dioctanoate (3.079 mmol, 2 g) was dissolved in dry DCM (20 ml). TFA was added at 0° C. to initiate a reaction. The reaction temperature was slowly allowed to warm to room temperature over for 30 minutes with stirring. Thin layer chromatography showed that the reaction was completed. The reaction product was concentrated under vacuum at 40° C. and the crude residue was diluted with DCM, and washed with a 10% $NaHCO_3$ solution. The aqueous layer was re-extracted with DCM, and the combined organic layers were washed with brine solution, dried over $Na_2SO_4$ and concentrated. The collected crude product was dissolved in dry DCM (20 ml) under nitrogen gas. Triphosgene (14.55 mmol, 4.32 g) was added and the reaction mixture was cooled to 0° C., and $Et_3N$ was added drop wise. The reaction mixture was stirred overnight at room temperature. Thin layer chromatography showed that the reaction was completed. DCM solvent was removed from the reaction mass by distillation under $N_2$. The reaction product was cooled to 0° C., diluted with DCM (20 ml), and 2-(dimethylamino)ethanethiol HCl (0.063 mol, 8.3 g) was added, followed by $Et_3N$ (dry). The reaction mixture was then stirred overnight at room temperature. Thin layer chromatography showed that the reaction was completed. The reaction product was diluted with 0.3 M HCl solution (20 ml), and the organic layer was separated. The aqueous layer was re-extracted with DCM, and the combined organic layers were washed with 10% $K_2CO_3$ aqueous solution 20 ml) and dried over anhydrous $Na_2SO_4$. Concentration of the solvent gave a crude mass of 10 gram. The crude compound was purified by silica gel column (100-200 mesh) using 3% MeOH/DCM. The yield was 1.4 g (75%)

Example 16

Synthesis of ATX-011 to ATX-030 and ATX-32

The synthesis of ATX-011 to ATX-30 follows the synthesis of Examples 1-15, by substituting appropriate starting ingredients for synthetic reactions described therein.

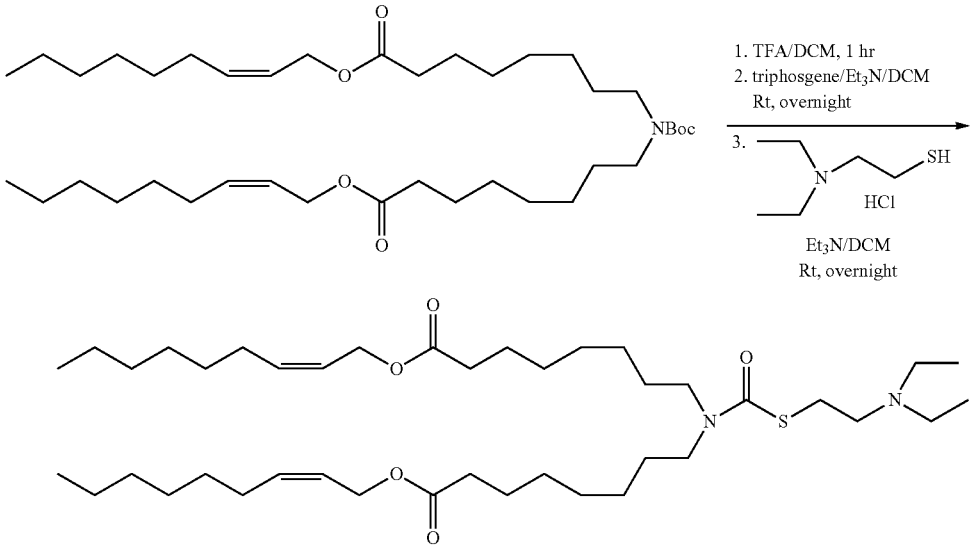

ATX-10

Example 17
Synthesis of ATX-031
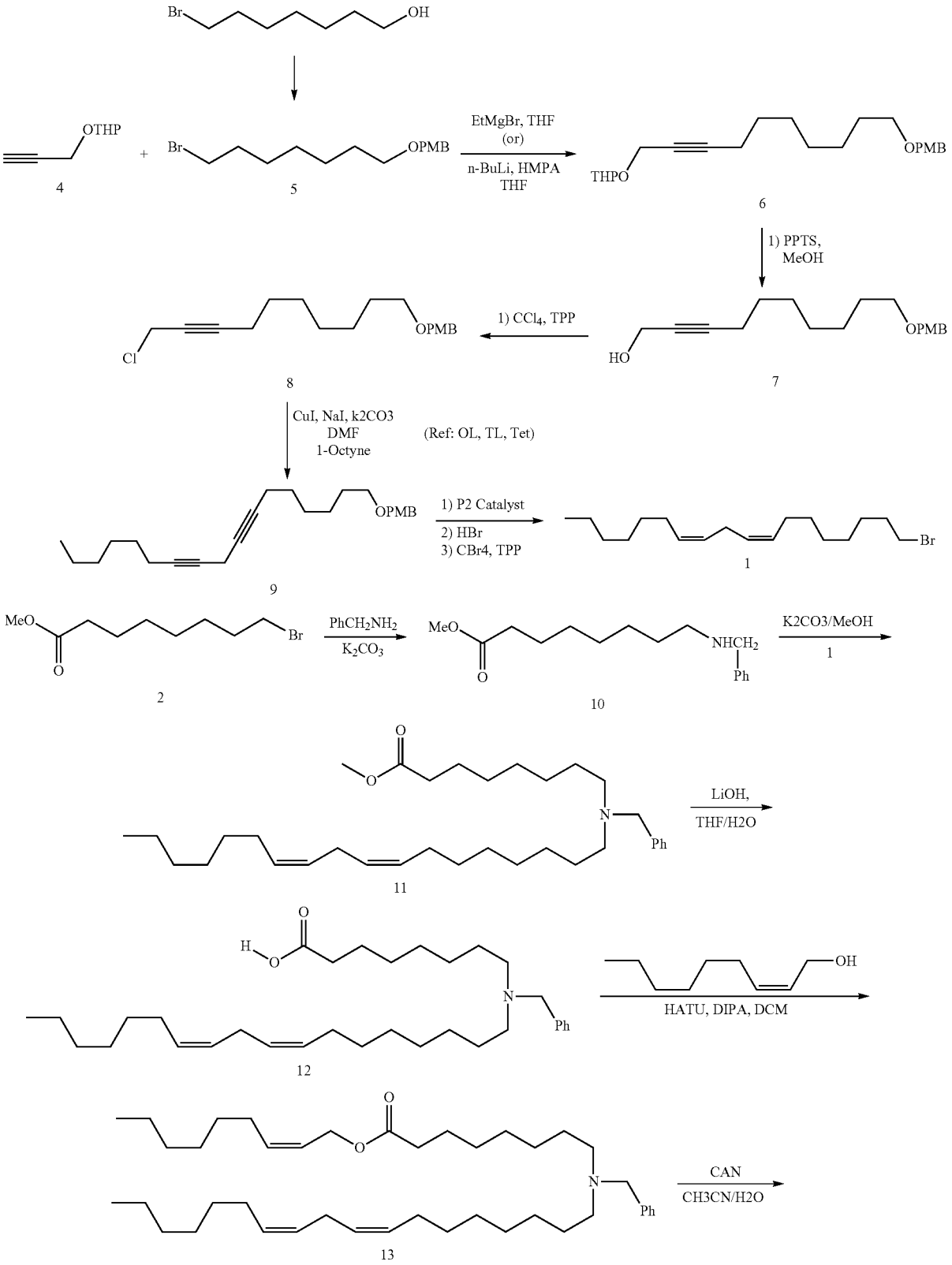

-continued

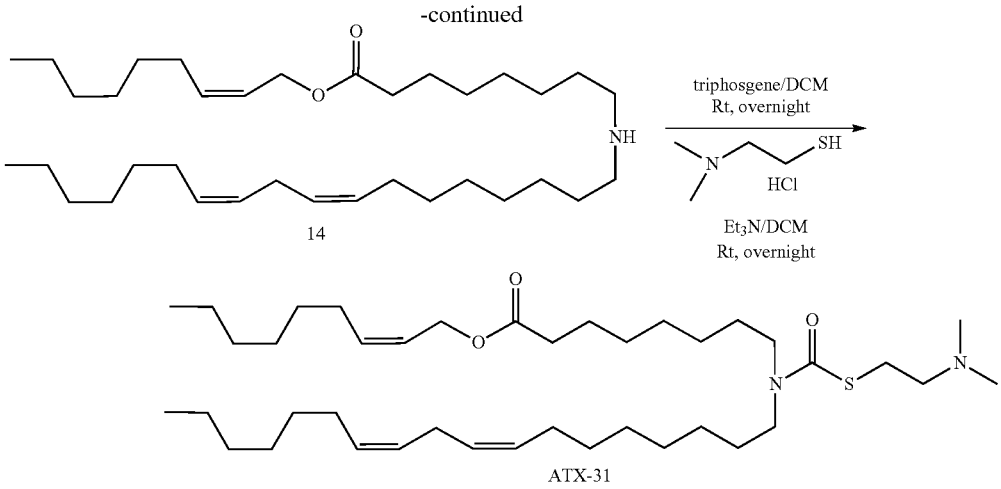

Example 19

In Vivo Mouse Factor VII Silencing

Using a liver-directed in vivo screen of the liposome libraries, a series of compounds were tested that facilitate high levels of siRNA mediated gene silencing in hepatocytes, the cells comprising the liver parenchyma. Factor VII, a blood clotting factor, is a suitable target gene for assaying functional siRNA delivery to liver. Because this factor is produced specifically in hepatocytes, gene silencing indicates successful delivery to parenchyma, as opposed to delivery to the cells of the reticulo-endothelial system (e.g., Kupffer cells). Furthermore, Factor VII is a secreted protein that can be readily measured in serum, obviating the need to euthanize animals. Silencing at the mRNA level can be readily determined by measuring levels of protein. This is because the protein's short half-life (2-5 hour). C57BL/6 mice (Charles River Labs) received either saline or siRNA in liposome formulations via tail vein injection at a volume of 0.006 ml/g. At 48 h after administration, animals were anesthetized by isofluorane inhalation and blood was collected into serum separator tubes by retroorbital bleed. Serum levels of Factor VII protein were determined in samples using a chromogenic assay (Biophen FVII, Aniara Corporation) according to manufacturers' protocols. A standard curve was generated using serum collected from saline-treated animals.

Figure 2:
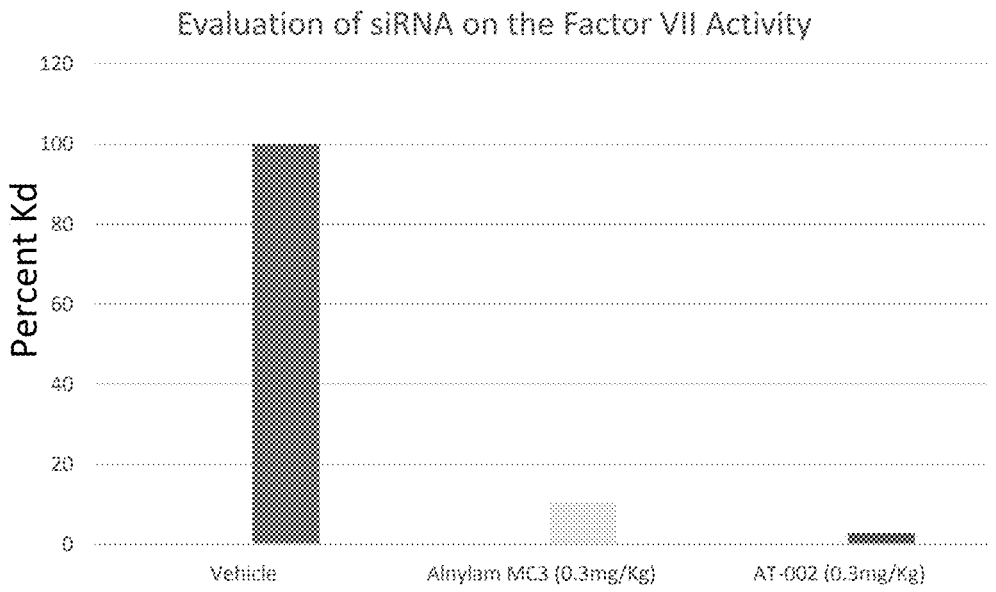
FIG. 2 shows an evaluation of the effect of siRNA of Factor VII activity based on the results shown in FIG. 2, and normalized to percentage knockdown compared to the vehicle alone.

Compositions with siRNA directed to Factor VIII were formulated with ATX-001, ATX-002, ATX-003, and ATX-547, and comparator samples NC1 and MC3 (Alnylam). These were injected into animals at 0.3 mg/kg and at 1 mg/kg. The siRNA encapsulated by MC3 (0.3 mg/kg), NC1 (0.3 mg/kg), ATX-547 (0.3 mg/kg), ATX-001 (0.3 and 1.0 mg/kg), ATX-002 (0.3 and 1.0 mg/kg), and ATX-003 (0.3 and 1.0 mg/kg) was measured for the ability to knockdown Factor VII in mouse plasma following administration of the siRNA formulation to C57BL6 mice. The results showed that ATX-001 and ATX-002 were most effective at 0.3 mg/kg, compared to controls (FIGS. 1 and 2).

Figure 3:
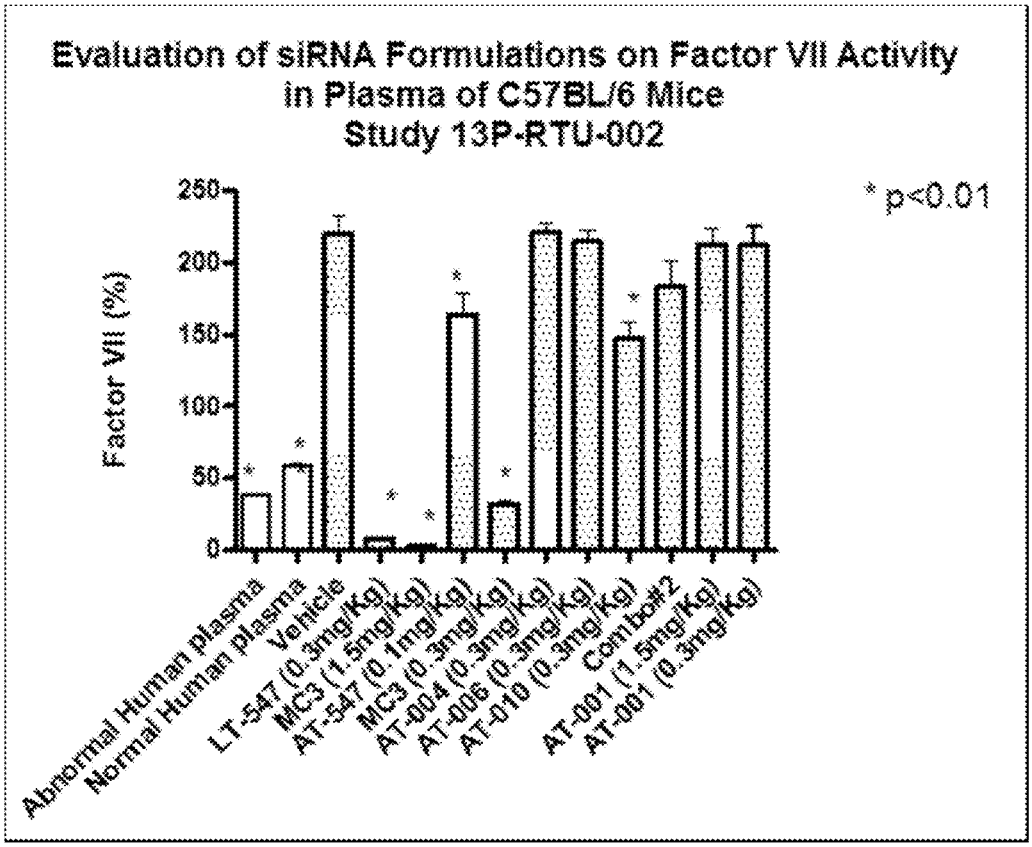
FIG. 3 shows the knockdown activity of siRNA encapsulated by different cationic lipids. The lipids include MC3 (0.3 and 1.5 mg/kg), NC1 (0.3 mg/kg), AT547 (0.1 and 0.3 mg/kg), AT004 (0.3), AT006 (0.3 and 1.0 mg/kg), ATX-010 (0.3 mg/kg), and AT001 (0.3 and 1.5 mg/kg). The amount of Factor VII knockdown in mouse plasma is shown following administration of the siRNA formulation to C57BL6 mice, compared to injection of vehicle alone. The amount of Factor VII in abnormal and normal human plasma is included as a control. Statistically significant decreases in Factor VII levels ($p<0.01$) is shown by an asterix (*).
Figure 4:
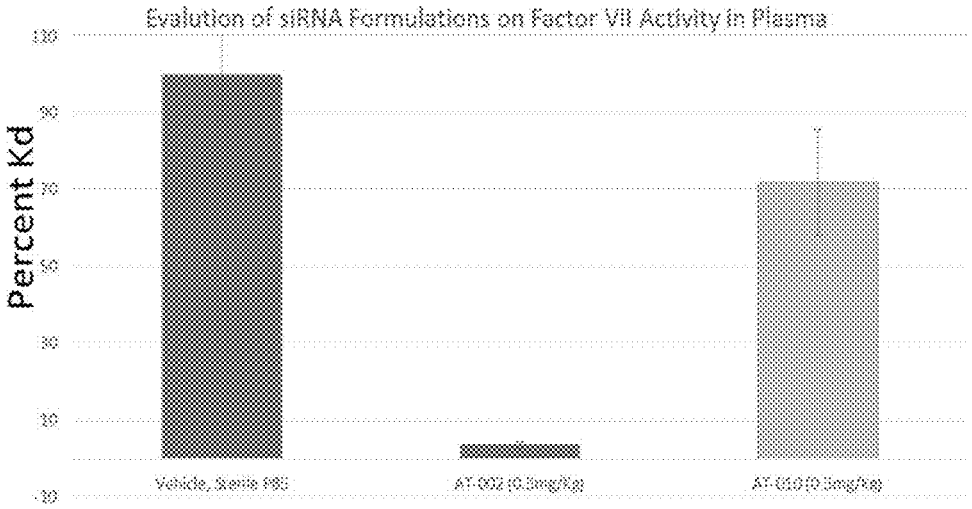
FIG. 4 shows an evaluation of the effect of siRNA of Factor VII activity based on the results shown in FIG. 2, and normalized to percentage knockdown compared to the vehicle alone.

The siRNA encapsulated MC3 (0.3 and 1.5 mg/kg), NC1 (0.3 mg/kg), ATX-547 (0.1 and 0.3 mg/kg), ATX-004 (0.3), ATX-006 (0.3 and 1.0 mg/kg), ATX-010 (0.3 mg/kg), and ATX-001 (0.3 and 1.5 mg/kg), was measured for Factor VII knockdown in mouse plasma following administration of the siRNA formulation to C57BL6 mice. The results showed that ATX-001 and ATX-010 were most effective (FIGS. 3 and 4). The knockdown activity of the exemplary compounds is shown for 0.3 mg/kg or at 0.05 mg/kg for ATX-018, ATX-019, and ATX-020 (Table 1).

What is claimed is:

[1. A compound of formula

1

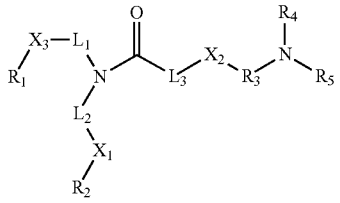

wherein $R_1$ and $R_2$ are the same or different, each a linear or branched alkyl consisting of 1 to 9 carbons, an alkenyl or alkynyl consisting of 2 to 11 carbons, or cholesteryl, $L_1$ and $L_2$ are the same or different, each a linear alkylene or alkenylene consisting of 5 to 18 carbons, $X_1$ is —CO—O— whereby -$L_2$-CO—O—$R_2$ is formed, $X_2$ is S or O, $X_3$ is —CO—O— whereby -$L_1$-CO—O—$R_1$ is formed, $L_3$ is a bond, $R_3$ is a linear or branched alkylene consisting of 1 to 6 carbons, and $R_4$ and $R_5$ are the same or different, each hydrogen or a linear or branched alkyl consisting of 1 to 6 carbons;

or a pharmaceutically acceptable salt thereof.]

[2. The compound of claim 1, wherein the $X_2$ is S.]

[3. The compound of claim 1, wherein the $R_3$ is ethylene.]

[4. The compound of claim 1, wherein the $R_3$ is n-propylene or isobutylene.]

[5. The compound of claim 1, wherein the $R_4$ and $R_5$ are separately methyl, ethyl, or isopropyl.]

[6. The compound of claim 1, wherein $L_1$ and $L_2$ are the same.]

[7. The compound of claim 1, wherein $L_1$ and $L_2$ differ.]

[8. The compound of claim 1, wherein $L_1$ or $L_2$ consists of a linear alkylene having seven carbons.]

[9. The compound of claim 1, wherein $L_1$ or $L_2$ consists of a linear alkylene having nine carbons.]

[10. The compound of claim 1, wherein $R_1$ and $R_2$ are the same.]

[11. The compound of claim 1, wherein $R_1$ and $R_2$ differ.]

[12. The compound of claim 10, wherein $R_1$ and $R_2$ each consists of an alkenyl.]

[13. The compound of claim 10, wherein $R_1$ and $R_2$ each consists of an alkyl.]

[14. The compound of claim 12, wherein the alkenyl consists of a single double bond.]

[15. The compound of claim 10, wherein $R_1$ or $R_2$ consists of nine carbons.]

[16. The compound of claim 10, wherein $R_1$ or $R_2$ consists of eleven carbons.]

[17. The compound of claim 10, wherein $R_1$ or $R_2$ consists of seven carbons.]

[18. The compound of claim 1, wherein $L_3$ is a bond, $R_3$ is ethylene, $X_2$ is S, and $R_4$ and $R_5$ are each methyl.]

[19. The compound of claim 1, wherein $L_3$ is a bond, $R_3$ is n-propylene, $X_2$ is S, $R_4$ and $R_5$ are each methyl.]

[20. The compound of claim 1, wherein $L_3$ is a bond, $R_3$ is ethylene, $X_2$ is S, and $R_4$ and $R_5$ are each ethyl.]

[21. The compound of claim 1, selected from the group consisting of the compounds of formula ATX-001 to ATX-028, and ATX-031

ATX-002

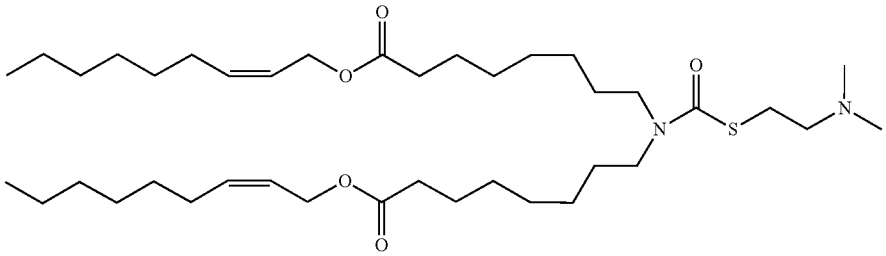

ATX-003

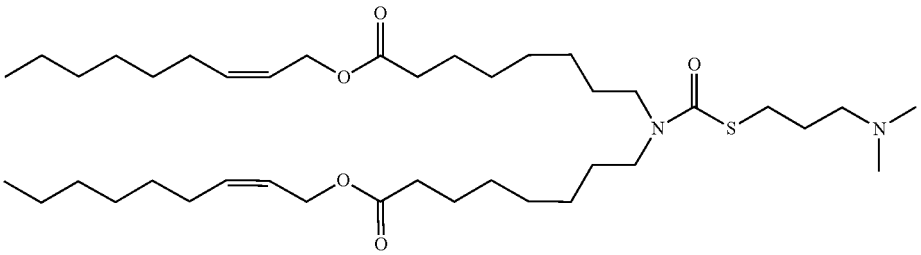

ATX-009

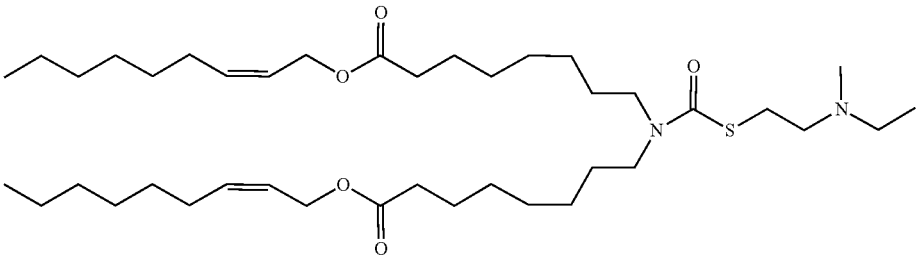

ATX-010
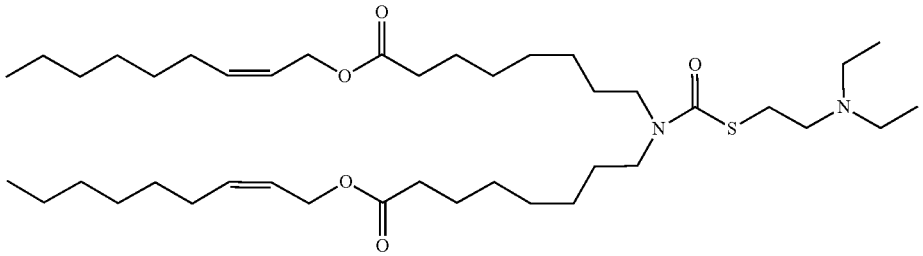
ATX-011
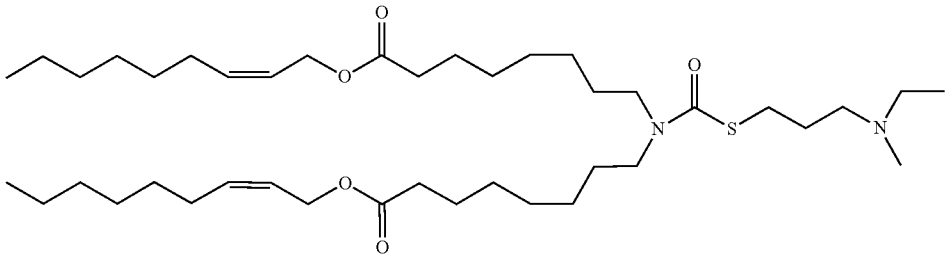
ATX-012
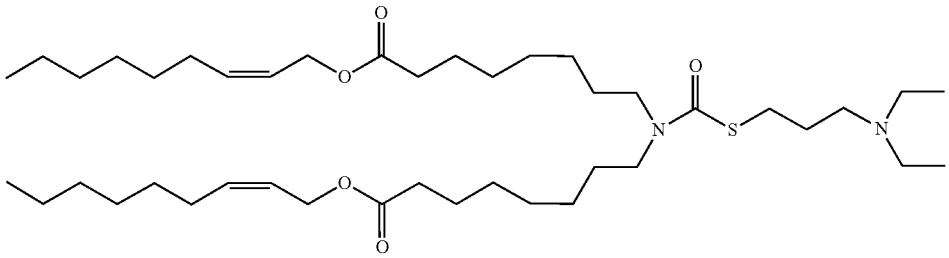
ATX-013
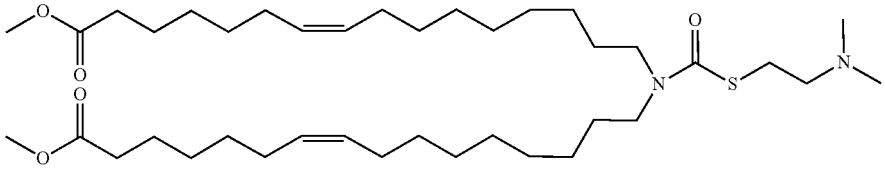
ATX-105
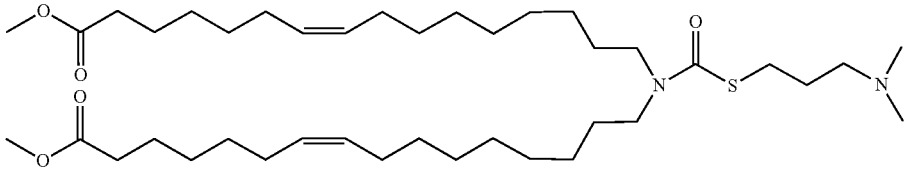

ATX-017
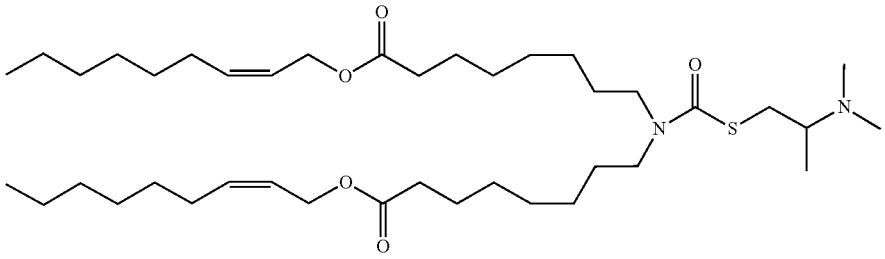
ATX-018
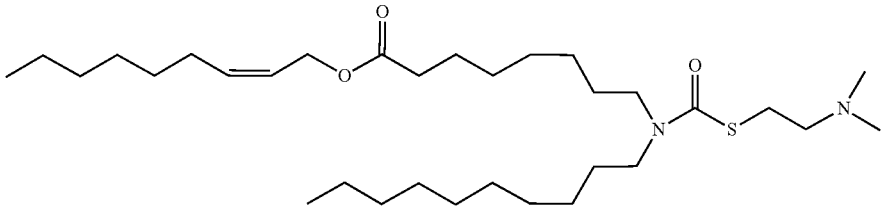
ATX-019
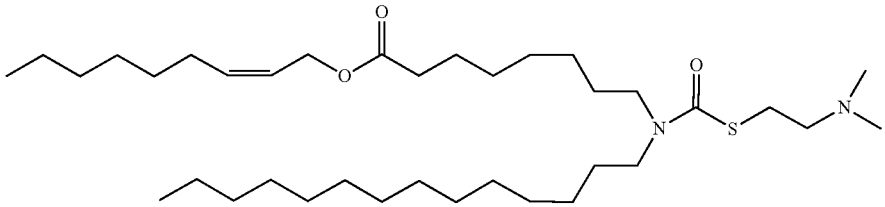
ATX-020
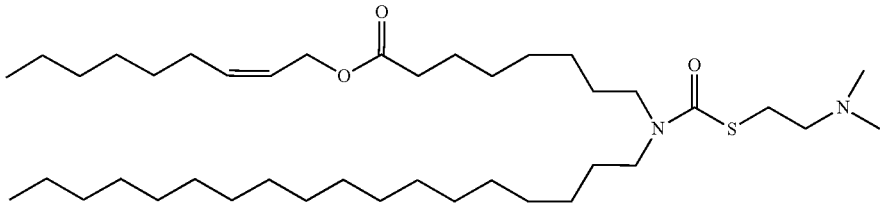
ATX-022
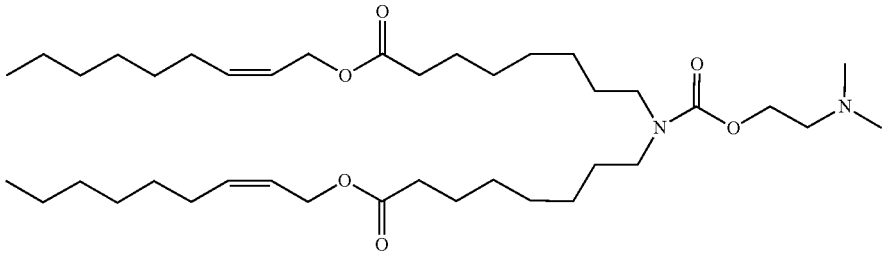

ATX-024
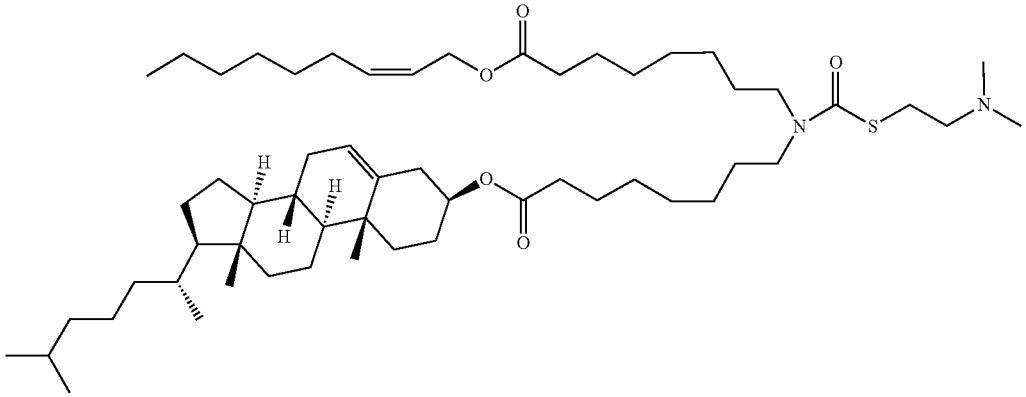
ATX-025
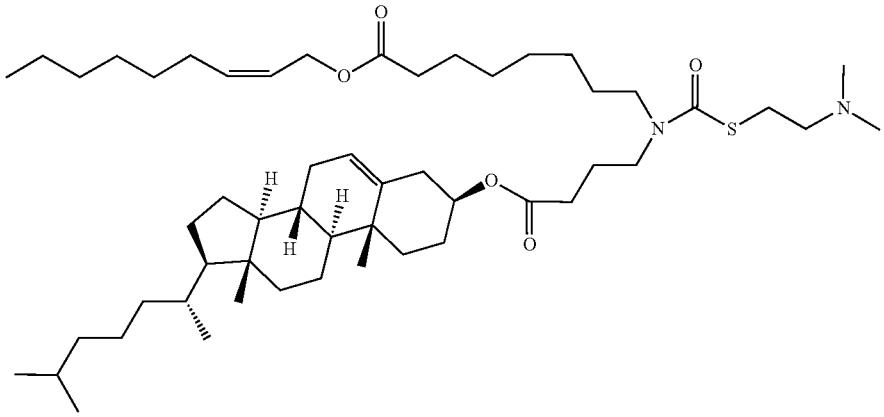
40
ATX-015
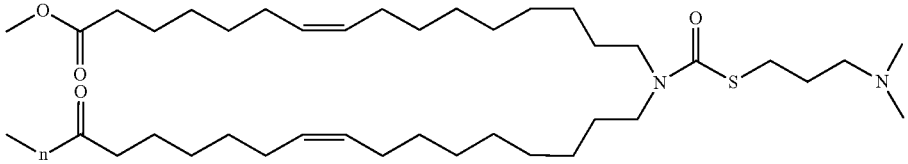
ATX-026
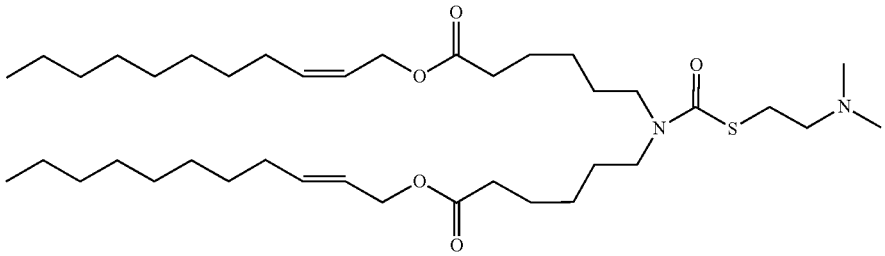

ATX-031

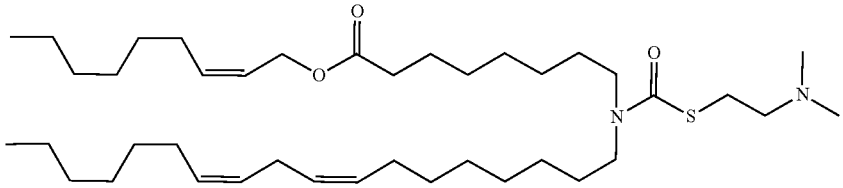

ATX-019

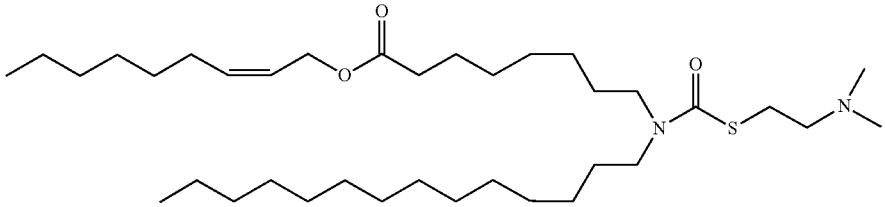

]

[22. A compound of formula I

1

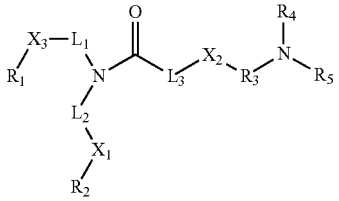

wherein $R_1$ and $R_2$ are the same or different, each a linear or branched alkyl consisting of 1 to 9 carbons, an alkenyl or alkynyl consisting of 2 to 11 carbons, or cholesteryl, $L_1$ and $L_2$ are the same or different, each a linear alkylene or alkenylene consisting of 3 or 4 carbons, $X_1$ is —CO—O— whereby -$L_2$-CO—O—$R_2$ is formed, $X_2$ is S or O, $X_3$ is —CO—O— whereby -$L_1$-CO—O—$R_1$ is formed, $L_3$ is a bond, $R_3$ is a linear or branched alkylene consisting of 1 to 6 carbons, and $R_4$ and $R_5$ are the same or different, each hydrogen or a linear or branched alkyl consisting of 1 to 6 carbons;

or a pharmaceutically acceptable salt thereof.]

[23. The compound of claim 22 consisting of the compound of formula ATX-029

ATX-029

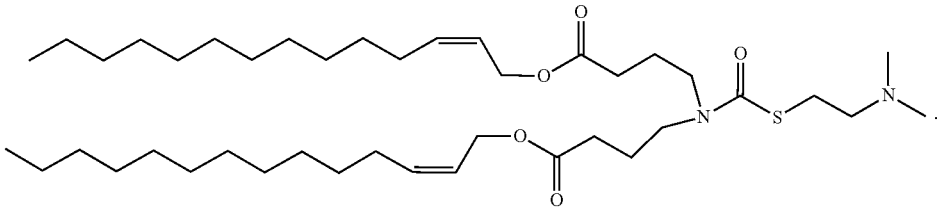

]

*24. A compound of formula 1:*

*1*

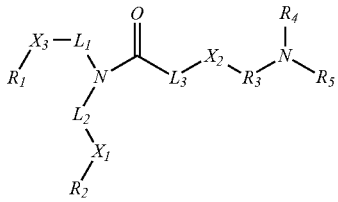

*wherein:*

$R_1$ *and* $R_2$ *are different and are each a linear or branched alkyl consisting of 1 to 9 carbons, an alkenyl consisting of 2 to 11 carbons, alkynyl consisting of 2 to 11 carbons, or cholesteryl,*

$L_1$ *and* $L_2$ *are the same or different, and are each a linear alkylene or alkenylene consisting of 5 to 18 carbons,*

$X_1$ *is —CO—O— whereby -*$L_2$*-CO—O—*$R_2$ *is formed,*

$X_2$ *is S or O,*

$X_3$ *is —CO—O— whereby -*$L_1$*-CO—O—*$R_1$ *is formed,*

$L_3$ *is a bond,*

$R_3$ *is a linear or branched alkylene consisting of 1 to 6 carbons, and*

$R_4$ *and* $R_5$ *are the same or different, and are each hydrogen or a linear or branched alkyl consisting of 1 to 6 carbons;*

*or a pharmaceutically acceptable salt thereof.*

*25. The compound of claim 24, wherein the alkenyl of* $R_1$ *and* $R_2$ *each consists of a single double bond.*

*26. A compound of formula 1:*

1

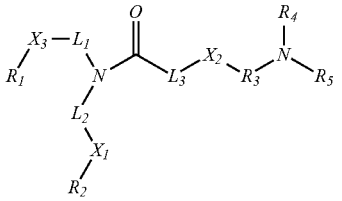

*wherein:*

$R_1$ *and* $R_2$ *are the same and are each a linear or branched alkyl consisting of 1 to 9 carbons, an alkynyl consisting of 2 to 11 carbons, or cholesteryl,*

$L_1$ *and* $L_2$ *are the same or different, each a linear alkylene or alkenylene consisting of 5 to 18 carbons,*

$X_1$ *is —CO—O— whereby -*$L_2$*-CO—O—*$R_2$ *is formed,*

$X_2$ *is S or O,*

$X_3$ *is —CO—O— whereby -*$L_1$*-CO—O—*$R_1$ *is formed,*

$L_3$ *is a bond,*

$R_3$ *is a linear or branched alkylene consisting of 1 to 6 carbons, and*

$R_4$ *and* $R_5$ *are the same or different, each hydrogen or a linear or branched alkyl consisting of 1 to 6 carbons;*

*or a pharmaceutically acceptable salt thereof.*

*27. The compound of claim 26, wherein the* $X_2$ *is S.*

*28. The compound of claim 26, wherein the* $R_3$ *is ethylene.*

*29. The compound of claim 26, wherein the* $R_3$ *is n-propylene or isobutylene.*

*30. The compound of claim 26, wherein the* $R_4$ *and* $R_5$ *are separately methyl, ethyl, or isopropyl.*

*31. The compound of claim 26, wherein* $L_1$ *and* $L_2$ *are the same.*

*32. The compound of claim 26, wherein* $L_1$ *and* $L_2$ *differ.*

*33. The compound of claim 26, wherein* $L_1$ *or* $L_2$ *consists of a linear alkylene having seven carbons.*

*34. The compound of claim 26, wherein* $L_1$ *or* $L_2$ *consists of a linear alkylene having nine carbons.*

*35. The compound of claim 26, wherein* $R_1$ *and* $R_2$ *each consists of an alkyl.*

*36. The compound of claim 26, wherein* $R_1$ *and* $R_2$ *each consists of nine carbons.*

*37. The compound of claim 26, wherein* $R_1$ *and* $R_2$ *each consists of eleven carbons.*

*38. The compound of claim 26, wherein* $R_1$ *and* $R_2$ *each consists of seven carbons.*

* * * * *